(12) United States Patent
Coppens et al.

(10) Patent No.: US 11,206,996 B2
(45) Date of Patent: Dec. 28, 2021

(54) PATIENT TROLLEY AND PATIENT TRANSFER DEVICE

(71) Applicant: QFIX SYSTEMS, LLC, Avondale, PA (US)

(72) Inventors: Daniel Coppens, Avondale, PA (US); Richard Herrschaft, West Chester, PA (US); Sean McGrenaghan, West Chester, PA (US); Franklin Ports, Jr., Conowingo, MD (US)

(73) Assignee: QFIX SYSTEMS, LLC, Avondale, PA (US)

( * ) Notice: Subject to any disclaimer, the term of this patent is extended or adjusted under 35 U.S.C. 154(b) by 250 days.

(21) Appl. No.: 15/767,517

(22) PCT Filed: Oct. 14, 2016

(86) PCT No.: PCT/US2016/057123
§ 371 (c)(1),
(2) Date: Apr. 11, 2018

(87) PCT Pub. No.: WO2017/066628
PCT Pub. Date: Apr. 20, 2017

(65) Prior Publication Data
US 2018/0296406 A1 Oct. 18, 2018

Related U.S. Application Data

(60) Provisional application No. 62/241,403, filed on Oct. 14, 2015, provisional application No. 62/241,400, filed on Oct. 14, 2015.

(51) Int. Cl.
*A61B 5/055* (2006.01)
*A61G 1/02* (2006.01)
(Continued)

(52) U.S. Cl.
CPC ............ *A61B 5/055* (2013.01); *A61G 1/02* (2013.01); *A61G 1/0287* (2013.01); *A61G 7/051* (2016.11);
(Continued)

(58) Field of Classification Search
CPC .... A61B 5/0555; A61G 7/051; A61G 7/1001; A61G 7/0508; A61G 1/0287; A61G 1/02;
(Continued)

(56) References Cited

U.S. PATENT DOCUMENTS 3,304,116 A    2/1967  Stryker
3,344,445 A *  10/1967 Crawford ............. A61G 7/0524
                                                     5/430
(Continued)

FOREIGN PATENT DOCUMENTS

CN    1415272 A    5/2003
CN    2614662 Y    5/2004
(Continued)

OTHER PUBLICATIONS

European Communication for European Application No. 16788342.0, dated Nov. 21, 2019, 6 pages.
(Continued)

*Primary Examiner* — Myles A Throop
(74) *Attorney, Agent, or Firm* — RatnerPrestia

(57) ABSTRACT

A patient trolley configured for transporting a patient to a target modality includes a top portion having a top surface and an overhang area along at least one side of the top portion, a bottom portion supporting the top portion, and a side rail coupled to the top portion for movement between a deployed position and a stowed position. The patient trolley is configured to dock adjacent the target modality such that the overhang area is capable of extending over at least a portion of the target modality. The patient trolley may be
(Continued)

combined with a patient transfer device to facilitate transfer of a patient from the top surface of the patient trolley to the patient support surface of the target modality. Methods of docking the patient trolley adjacent a target modality and transferring a patient from the patient trolley to the target modality are also provided.

13 Claims, 15 Drawing Sheets

(51) Int. Cl.
*A61G 7/10* (2006.01)
*A61G 7/05* (2006.01)

(52) U.S. Cl.
CPC .......... *A61G 7/0508* (2016.11); *A61G 7/1001* (2013.01); *A61G 7/103* (2013.01); *A61G 7/1046* (2013.01); *A61G 7/0515* (2016.11); *A61G 7/0519* (2016.11); *A61G 2210/50* (2013.01)

(58) Field of Classification Search
CPC .... A61G 7/1025; A61G 7/103; A61G 7/1046; A61G 2210/50; A61G 7/0515; A61G 7/0519
See application file for complete search history.

(56) References Cited

U.S. PATENT DOCUMENTS

| | | | |
|---|---|---|---|
| 4,175,783 A | 11/1979 | Pioth | |
| 4,259,756 A * | 4/1981 | Pace | A61G 7/1046 5/425 |
| 4,653,129 A * | 3/1987 | Kuck | A61G 1/04 5/428 |
| 4,947,496 A * | 8/1990 | Connolly | A61G 7/008 5/430 |
| 4,949,410 A * | 8/1990 | Failor | A61G 5/006 5/425 |
| 4,985,946 A * | 1/1991 | Foster | A61G 7/00 5/427 |
| 5,179,744 A * | 1/1993 | Foster | A61G 7/00 5/185 |
| 5,187,824 A * | 2/1993 | Stryker | A61G 7/0507 5/430 |
| 5,522,100 A * | 6/1996 | Schilling | A61G 7/0507 5/185 |
| 5,604,942 A * | 2/1997 | Allevato | A61G 7/0507 5/428 |
| 5,733,247 A | 3/1998 | Fallon | |
| 6,092,248 A | 7/2000 | Boemmel et al. | |
| D456,751 S * | 5/2002 | Williams | D12/132 |
| 6,936,030 B1 | 8/2005 | Pavlik et al. | |
| 7,263,733 B2 | 9/2007 | Fujita et al. | |
| 8,239,986 B2 * | 8/2012 | Heimbrock | A61G 7/0507 5/425 |
| 8,294,588 B2 | 10/2012 | Fisher et al. | |
| 8,370,978 B2 * | 2/2013 | Duvert | A61G 7/053 5/428 |
| 8,656,528 B2 | 2/2014 | Perelman et al. | |
| 9,021,634 B2 | 5/2015 | Goto et al. | |
| 9,144,409 B1 | 9/2015 | Ocel et al. | |
| 9,179,880 B2 | 11/2015 | Coppens et al. | |
| 9,351,893 B2 | 5/2016 | Jei | |
| 2001/0012914 A1 | 8/2001 | Kuth et al. | |
| 2003/0070226 A1 | 4/2003 | Heimbrock | |
| 2003/0159212 A1 | 8/2003 | Patrick et al. | |
| 2004/0168254 A1 | 9/2004 | Rabska et al. | |
| 2006/0059621 A1 | 3/2006 | Poulos et al. | |
| 2006/0195984 A1 | 9/2006 | HakamuiN et al. | |
| 2007/0089235 A1 | 4/2007 | Devinat et al. | |
| 2008/0127416 A1 | 6/2008 | Tigwell | |
| 2008/0173218 A1 | 7/2008 | Wang et al. | |
| 2009/0024020 A1 | 1/2009 | Swaminathan et al. | |
| 2009/0049613 A1 | 2/2009 | Dippl et al. | |
| 2009/0232271 A1 | 9/2009 | Sendai | |
| 2009/0249544 A1 * | 10/2009 | Palay | A61G 5/14 5/83.1 |
| 2011/0009903 A1 | 1/2011 | Estrada | |
| 2011/0163885 A1 | 7/2011 | Poulos et al. | |
| 2011/0237960 A1 | 9/2011 | Rantala | |
| 2012/0000016 A1 | 1/2012 | Dong et al. | |
| 2012/0023666 A1 * | 2/2012 | Heimbrock | A61G 7/053 5/428 |
| 2012/0102649 A1 * | 5/2012 | O'Keefe | A61G 7/018 5/618 |
| 2013/0150656 A1 | 6/2013 | Falk et al. | |
| 2013/0239327 A1 * | 9/2013 | Lemonnier | A61G 7/0507 5/428 |
| 2013/0316624 A1 | 11/2013 | Diehl et al. | |
| 2013/0340167 A1 * | 12/2013 | Karwal | A61G 7/005 5/611 |
| 2014/0090168 A1 * | 4/2014 | Coppens | A61G 7/1025 5/81.1 R |
| 2014/0187379 A1 | 7/2014 | Chen et al. | |
| 2015/0135433 A1 * | 5/2015 | Jei | A61G 1/02 5/81.1 HS |
| 2016/0213538 A1 * | 7/2016 | Lus | A61G 7/0507 |
| 2016/0244184 A1 | 8/2016 | Alderman et al. | |
| 2016/0270614 A1 | 9/2016 | Kawamura et al. | |
| 2017/0055717 A1 * | 3/2017 | Guthrie | A61G 7/051 |
| 2018/0168899 A1 * | 6/2018 | Newkirk | A61G 7/1015 |

FOREIGN PATENT DOCUMENTS

| | | |
|---|---|---|
| CN | 2820084 Y | 9/2006 |
| CN | 1969747 A | 5/2007 |
| CN | 1990062 A | 7/2007 |
| CN | 101032424 A | 9/2007 |
| CN | 101150988 A | 3/2008 |
| CN | 101375173 A | 2/2009 |
| CN | 201192420 Y | 2/2009 |
| CN | 101460099 A | 6/2009 |
| CN | 101548194 A | 9/2009 |
| CN | 101711700 A | 5/2010 |
| CN | 101715309 A | 5/2010 |
| CN | 201519238 U | 7/2010 |
| CN | 102281855 A | 12/2011 |
| CN | 102309321 A | 1/2012 |
| CN | 202161495 U | 3/2012 |
| CN | 102551978 A | 7/2012 |
| CN | 202409301 U | 9/2012 |
| CN | 202875639 U | 4/2013 |
| CN | 103462689 A | 12/2013 |
| CN | 203468903 U | 3/2014 |
| CN | 203564433 U | 4/2014 |
| CN | 103892910 A | 7/2014 |
| CN | 104068982 A | 10/2014 |
| CN | 204033627 U | 12/2014 |
| CN | 204050076 U | 12/2014 |
| CN | 104582666 A | 4/2015 |
| CN | 204379573 U | 6/2015 |
| DE | 202007004182 U1 | 5/2007 |
| GB | 975226 | 11/1964 |
| WO | 2013153493 A1 | 10/2013 |
| WO | 2014055655 A1 | 4/2014 |
| WO | 2015023731 A2 | 2/2015 |

OTHER PUBLICATIONS

Chinese Office Action for Chinese Application No. 201680072417.6, dated Jul. 2, 2019, with translation, 33 pages.
Non Final Office Action for U.S. Appl. No. 15/767,715, dated Dec. 30, 2019, 14 pages.
Non Final Office Action for U.S. Appl. No. 15/767,715, dated Oct. 21, 2019, 63 pages.
Chinese Office Action for Chinese Application No. 201680071020.5, dated Apr. 3, 2020, with translation, 19 pages.

(56) References Cited

OTHER PUBLICATIONS

Final Office Action for U.S. Appl. No. 15/767,715, dated May 26, 2020, 32 pages.
Communication Pursuant to Article 94(3) for European Application No. 16 788 343.8, dated Mar. 7, 2019, 7 pages.
Extended European Search Report for European Application No. 19 156 260.2, dated Mar. 20, 2019, 8 pages.
Chinese Office Action for Chinese Application No. 201680071020.5, dated Jul. 1, 2019 with translation, 19 pages.
Decision of Rejection for Chinese Application No. 201680072417.6, dated Nov. 3, 2020, with translation, 36 pages.
European Communication pursuant to Article 94(3) for European Application No. 19 156 260.2, dated Apr. 20, 2020, 6 pages.
Chinese Office Action for Chinese Application No. 201680072417.6, dated Apr. 3, 2020, with translation, 45 pages.
International Search Report and Written Opinion for International Application No. PCT/US2016/057123, dated Jun. 7, 2017, 22 pages.
International Preliminary Report on Patentability for International Application No. PCT/US2016/057108, dated Apr. 17, 2018, 8 pages.
International Search Report and Written Opinion for International Application No. PCT/US2016/057108, dated Jan. 24, 2017, 9 pages.
Chinese Office Action for Chinese Application No. 201680071020.5, dated Oct. 23, 2020, with translation, 21 pages.
Chinese Office Action for Chinese Application No. 201911155907.4, dated Dec. 2, 2020 with translation. 19 pages.
Chinese Office Action for Chinese Application No. 201680072417.6, dated Apr. 1, 2021 with translation, 21 pages. 2021
Notice of Allowance for U.S. Appl. No. 15/767,715, dated Feb. 11, 2021, 23 pages.

\* cited by examiner

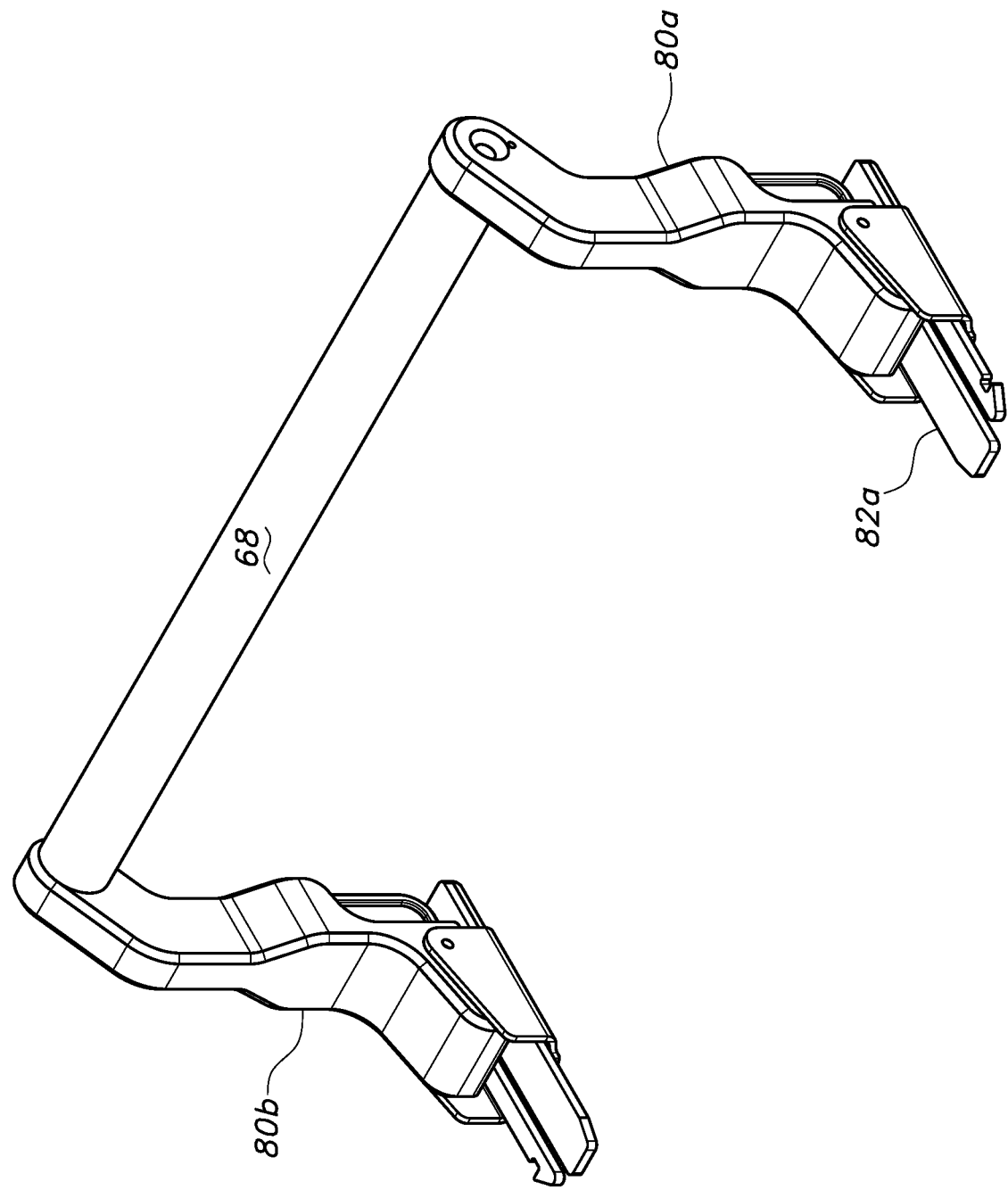

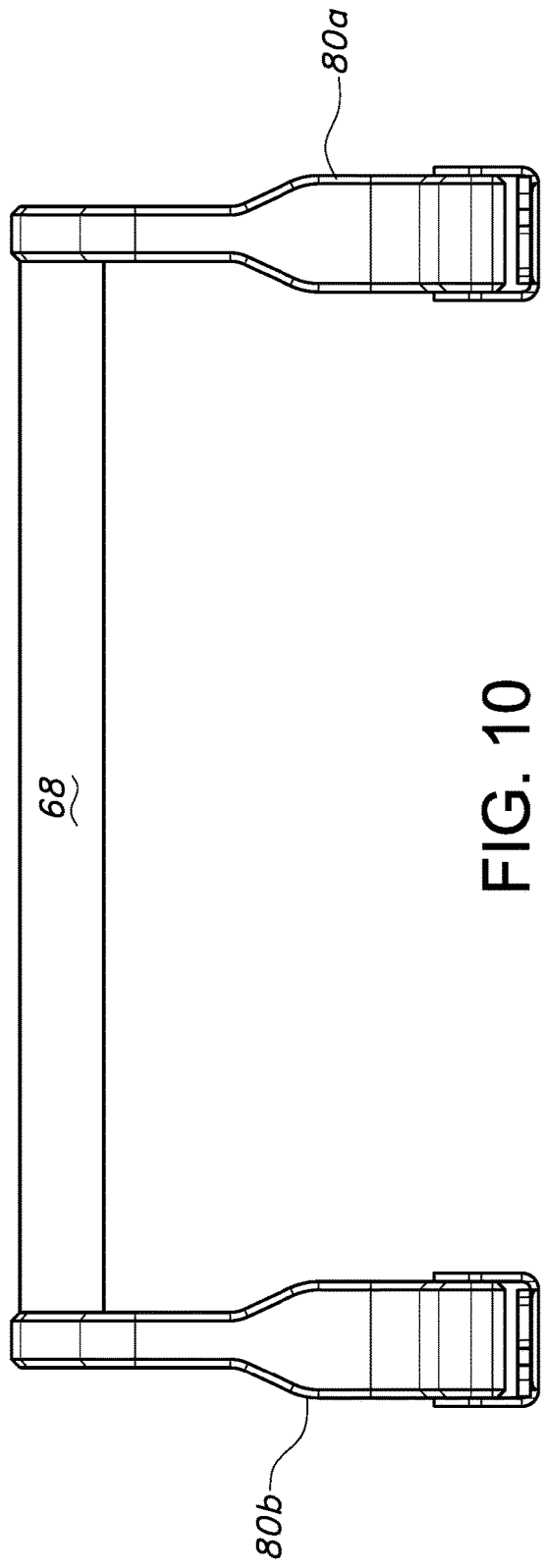
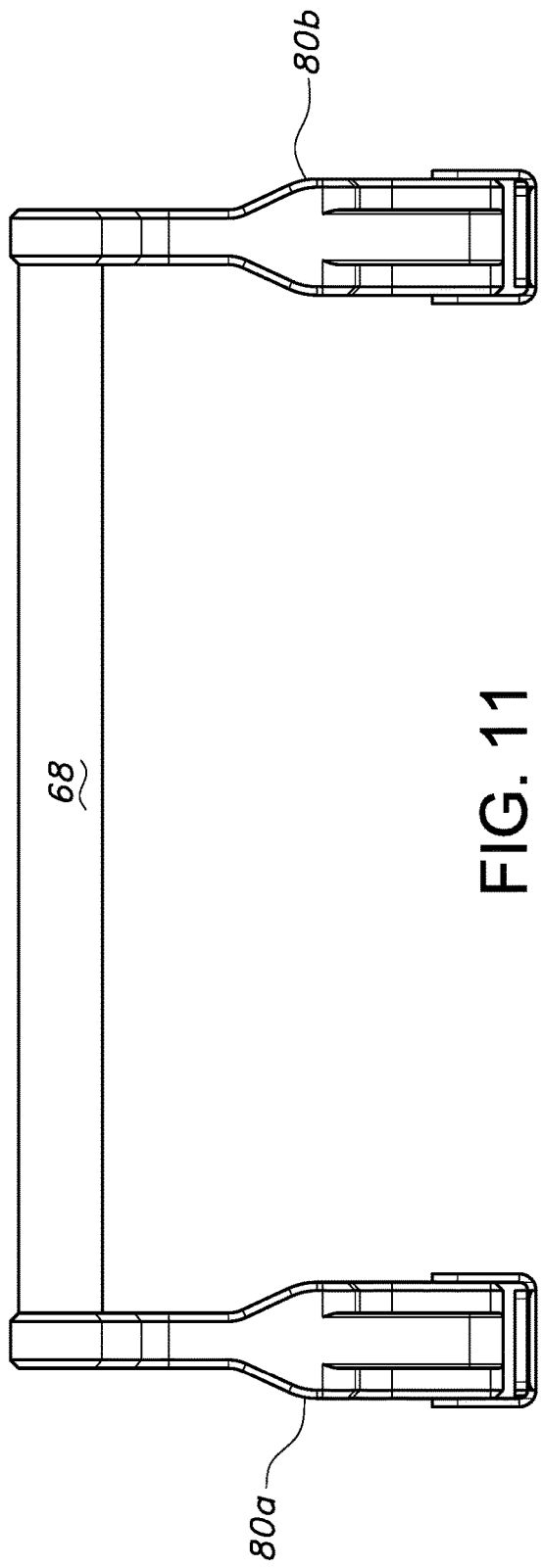

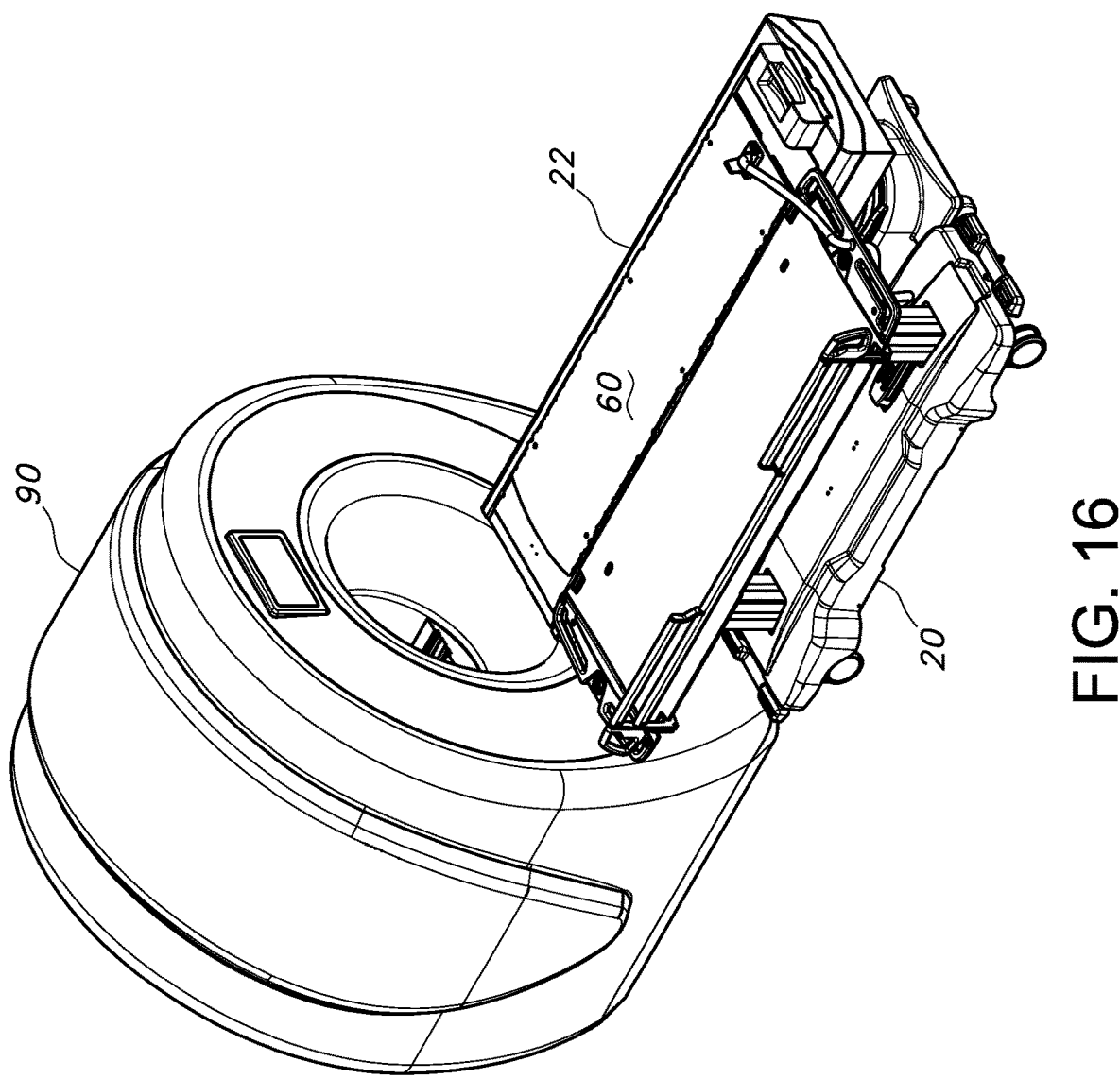

PATENT TROLLEY AND PATIENT TRANSFER DEVICE

CROSS REFERENCE TO RELATED APPLICATIONS

This application is a U.S. National Phase Application of PCT International Application PCT/US2016/057123, filed on Oct. 14, 2016, which claims the benefit of U.S. provisional patent application entitled "PATIENT TROLLEY AND PATIENT TRANSFER DEVICE," which was filed on Oct. 14, 2015 and assigned Ser. No. 62/241,400, and U.S. provisional patent application entitled "MRI COMPATIBLE PATIENT TROLLEY," which was filed on Oct. 14, 2015 and assigned Ser. No. 62/241,403. The entire contents of the foregoing provisional applications are incorporated herein by reference in their entirety.

FIELD OF THE INVENTION

The present invention generally relates to patient trolleys for transporting patients and patient transfer devices for providing safe transfer of a patient from the patient trolley to a target modality during medical procedures, and associated systems and methods.

BACKGROUND OF THE INVENTION

Patient trolleys are used frequently in hospitals and treatment centers to transport patients to various locations within the facility. When the patient requires therapy or diagnostic imaging, the patient trolleys are used to deliver the patient in proximity to certain target modalities. Target modalities may include various patient support surfaces associated with machines, such as CT, MR, and PET, an operating table, a hospital bed, an OR table, a radiotherapy treatment system, robotic surgical arms, etc. Patient trolleys are expected to safely transport a patient to and from various target modalities. Often these patients must be immobilized to maintain positional accuracy and consistency from one modality to the next.

In order to transfer a patient from the top surface of a patient trolley to the surface of a target modality, patient transfer devices are commonly used. For patients that are not ambulatory and are expected to remain lying down, such as in a supine, prone, or recumbent position, patient trolley operators must transport the patient trolley to a location that is near to the surface of the target modality and transfer the patient using the patient transfer device by sliding the patient transfer device from the top surface of the patient trolley to the top surface of the target modality.

A need exists for improved patient trolleys that not only provide safe transport of patients, but also facilitate easier patient transfer to target modalities. These and other needs are addressed by the patient trolley and associated systems and methods of the present invention.

SUMMARY OF THE INVENTION

In one aspect of the present invention, a patient trolley configured for transporting a patient to a target modality and facilitating transfer of the patient from the trolley to a support surface of the target modality is provided, the patient trolley comprising:
  a top portion having a top width and a top surface extending across the top width, the top portion also having an overhang area along at least one side of the top portion;
  a bottom portion supporting the top portion, the bottom portion having a lateral wheel base width narrower than the top width; and
  a side rail coupled to the top portion for movement between a deployed position in which a top of the side rail extends above the top surface of the top portion of the patient trolley and a stowed position in which the top of the side rail is below the top surface of the top portion of the patient trolley, inward from the overhang area of the top portion of the patient trolley, and inboard laterally within a boundary defining a perimeter of the top surface;
wherein the top portion is laterally fixed relative to the bottom portion. The bottom portion may include a plurality of wheels and a cover. The patient trolley is configured to dock adjacent to the target modality such that the overhang area is capable of extending over at least a portion of the target modality and adjacent to the patient support surface of the target modality thus placing the tops surfaces of the trolley and target modality in a substantially parallel configuration. The patient trolley may also be configured to satisfy the balance requirements of subclause 9.4.3.1 of IEC 60601-1 3rd Edition. A ratio of the top width to the lateral wheel base width may be at least 1.2:1, more preferably at least 1.25:1, most preferably at least 1.35:1. The lateral wheel base width of the patient trolley may also be at most 76 cm, more preferably at most 56 cm. The side rail may have a maximum height and a length and at least one section of the length having a reduced height, the reduced height being less than the maximum height.

In another aspect of the invention, a patient transfer system configured for transporting a patient to a target modality and facilitating transfer of the patient to a support surface of the target modality is provided. The patient transfer system may comprise:
  a patient trolley including
    a top portion having a top width and a top surface extending across the top width,
    an overhang area along at least one side of the top portion,
    a side rail coupled to the top portion for movement between a deployed position in which a top of the side rail extends above the top surface of the top portion of the patient trolley and a stowed position in which the top of the side rail is below the top surface of the top portion of the patient trolley and inward from the overhang area of the top portion of the patient trolley, and
    a bottom portion supporting the top portion, the bottom portion having a lateral wheel base width narrower than the top width;
  a patient transfer surface located on the top surface of the top portion, the patient transfer surface having, in a preferred embodiment, at least one gripping feature to manipulate the patient transfer surface; and
  a target modality having a support surface;
wherein the patient trolley is configured to dock adjacent the target modality when the side rail is in the stowed position such that the overhang area is capable of extending over at least a portion of the target modality and adjacent to the support surface of the target modality and facilitate transfer of the patient to the support surface of the target modality.

The side rail of the patient transfer system in the stowed position may be located below and within a boundary defining a perimeter of the top portion. The patient transfer system may also include a side rail having a maximum height and a length and at least one section of the length has a reduced height, the reduced height being less than the maximum height. At least one gripping feature, for example a handle, may be removably attached to the patient transfer surface and have a gripping portion extending to an elevation above the reduced height section of the side rail. The at least one section having a reduced height allows access to the handle when the side rail is in the deployed position.

In yet another aspect of the invention, a method of docking a patient trolley adjacent a target modality and transferring a patient from the patient trolley to the target modality is provided, the method comprising:
  positioning the patient trolley proximate to the target modality, the patient trolley including a top portion having a top width and a top surface extending across the top width;
  lowering a side rail of the patient trolley to an elevation below the top surface of the top portion of the patient trolley and inboard laterally such that the side rails is within the top width;
  adjusting an elevation of the top surface of the top portion of the patient trolley to generally correspond to an elevation of the support surface of the target modality; and
  docking a side of the patient trolley adjacent the target modality such that an overhang area along the side of the top portion of the patient trolley is capable of extending over at least a portion of the target modality and adjacent a support surface of the target modality, thereby positioning an edge of the top surface of the top portion of the patient trolley adjacent an edge of the support surface of the target modality; and
  gripping the patient transfer device and transferring the patient transfer device located on the top surface of the top portion of the patient trolley to the support surface of the target modality,
wherein during transfer of the patient transfer device, the patient transfer device is contacting at least one of the top surface of the trolley and the support surface of the target modality.

In another aspect of the invention, a patient transfer system configured for transporting a patient to and from a target modality and facilitating transfer of the patient to and from a support surface of the target modality is provided, the patient transfer system comprising a patient trolley and a patient transfer surface located on the top surface of the top portion, the patient transfer surface having at least one gripping feature.

BRIEF DESCRIPTION OF THE DRAWINGS

FIG. 9 is a top perspective view of a handle for a patient transfer device according to another aspect of the present invention;

FIG. 10 is a front view of the handle for the patient transfer device of FIG. 9;

FIG. 11 is a rear view of the handle for the patient transfer device of FIG. 9;

FIG. 16 is a top perspective view of the docked patient trolley of FIG. 15 with a patient transfer device located on the target surface of an MRI table in front of the MRI machine;

DETAILED DESCRIPTION OF THE INVENTION

Figure 1:
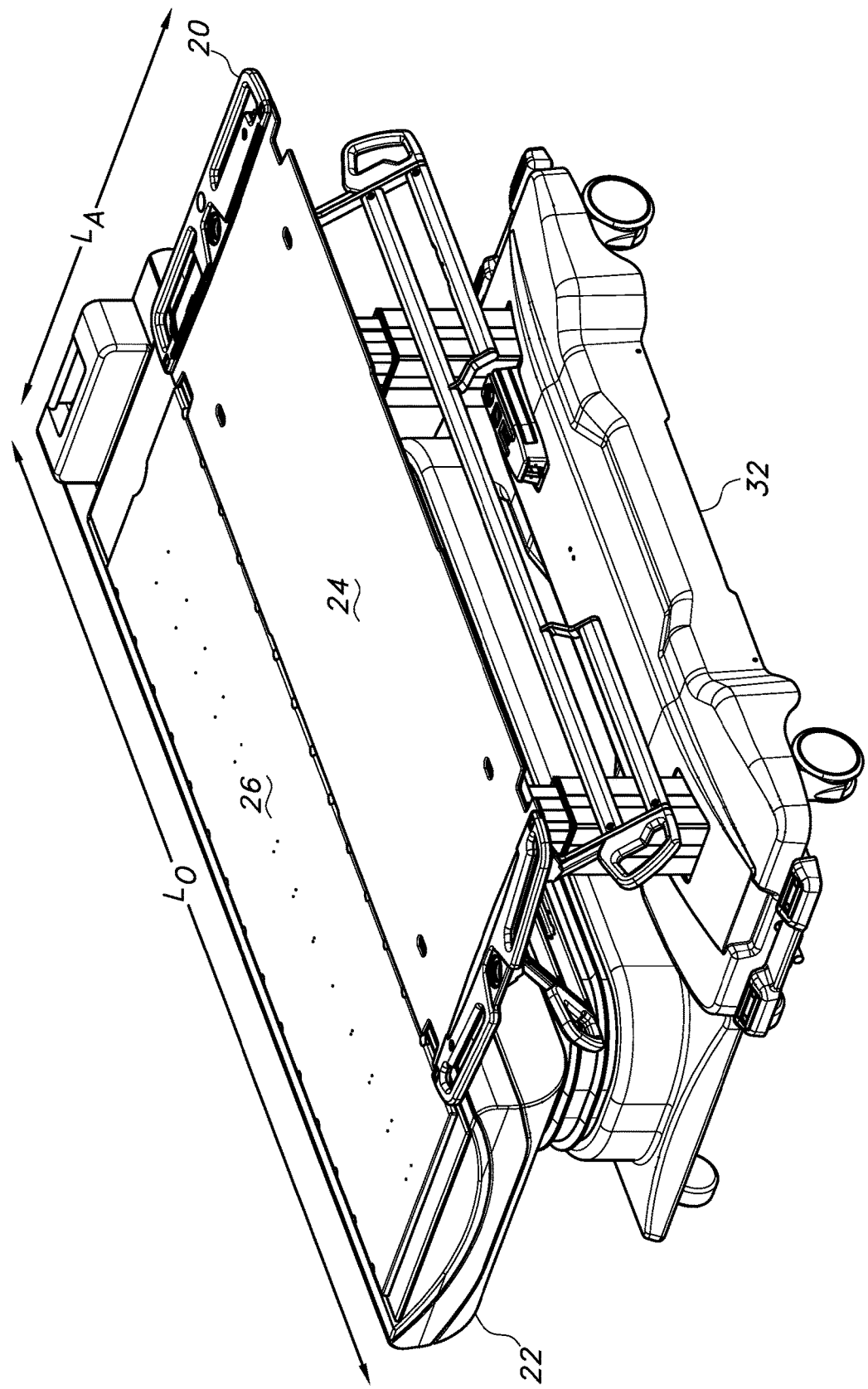
FIG. 1 is a top perspective view of a patient trolley according to an aspect of the present invention next to a target modality.

The invention will now be described by reference to exemplary embodiments and variations of those embodiments. Although the invention is illustrated and described herein with reference to specific embodiments, the invention is not intended to be limited to the details shown and described. Rather, various modifications may be made in the details within the scope and range of equivalents of the claims, without departing from the invention.

The configuration of a target modality makes it difficult to position a patient trolley, such that the top surfaces of the patient trolley and target modality are close enough to accomplish a safe patient transfer. It is preferable to position the location and height of the top surface of a patient trolley relative to the top surface of a target modality, such that the two surfaces are adjacent to each other with a minimum of distance between the two surfaces. This is often difficult when the target modality is the table for an MRI or CT machine. The width of the table of these machines can be much wider than the surface on which the patient is placed. These may have shrouds that extend up to 10 cm or more laterally beyond the edge of the patient support surface. To successfully transfer the patient between the trolley and the target modality, a method is required to overcome the shroud. The shroud presents a physical barrier for the trolley top and the target modality patient support surface from being placed adjacent to each other. This invention solves this problem without requiring any additional mechanism such as lateral shifting capability in the trolley top or rotating draw bridges as found in prior art.

It is possible to include extendable surfaces or movable top portions on the patient trolley. However, it is preferred to exclude such extendable surfaces or movable top portions. For example, extendable surfaces or movable top portions can result in a more complicated and expensive design of the patient trolley. Also, the mechanisms used to extend or move the patient surface of the trolley may fail or present additional safety risks. A shifting top surface of a patient trolley may also result in an imbalance increasing the probability that the patient trolley may tip over during patient transport.

Referring generally to the Figures, one aspect of the present invention provides a patient trolley 20 configured for transporting a patient to a target modality 22 and facilitating transfer of the patient from the trolley 20 to a support surface 26 of the target modality 22. The patient trolley 20 comprises a top portion having a top width and a top surface 24 extending across the top width, the top portion also having an overhang area 34 along at least one side of the top portion;

a bottom portion 30 supporting the top portion, the bottom portion having a lateral wheel base width, $B_w$, narrower than the top width; and a side rail 36a, 36b coupled to the top portion for movement between a deployed position in which a top of the side rail 36a, 36b extends above the top surface 24 of the top portion of the patient trolley 20 and a stowed position in which the top of the side rail 36a, 36b is below the top surface 24 of the top portion of the patient trolley 20 and inward from the overhang area 34 of the top portion of the patient trolley 20, wherein the top portion is laterally fixed relative to the bottom portion 30, and wherein the patient trolley 20 is configured to dock adjacent the target modality 22 such that the overhang area 34 is capable of extending over at least a portion of the target modality 22 and adjacent to the patient support surface 26 of the target modality 22. In the stowed position the side rail 36a, 36b may be located below and inboard laterally within a boundary defining a perimeter of the top surface 24. This position is desirable because the side rail will not physically prevent the trolley from being placed adequately close to the target modality, so that the top surface of the trolley may be adjacent to the top surface of the target modality and allow a transfer to be performed. There are many ways to implement a side rail that can be deployed and stowed satisfactorily to provide this functionality. For example, the side rail may be rotated around at least one axis or the side rail may be designed using a four bar linkage.

According to yet another aspect of the present invention, a patient transfer system configured for transporting a patient toward a target modality 22 and facilitating transfer of the patient to a support surface 26 of the target modality 22 is provided. The patient transfer system comprises a patient trolley 20 and a patient transfer surface 60 located on the top surface 24 of the top portion, the patient transfer surface 60 having at least one gripping feature 62a, 62b. The patient transfer system may further include the target modality 22.

Referring now to each of the figures more specifically, wherein like reference numerals used in the figures denote like parts throughout the various figures, a patient trolley 20 according to an embodiment of the present invention is illustrated in FIG. 1 next to a target modality table 22, which is in the form of an MRI machine. As used in the specification and the claims, the "longitudinal" direction is the lengthwise direction along the axis $L_O$ and the "lateral" direction is the widthwise direction along the axis $L_A$, as illustrated in FIG. 1.

Figure 2:
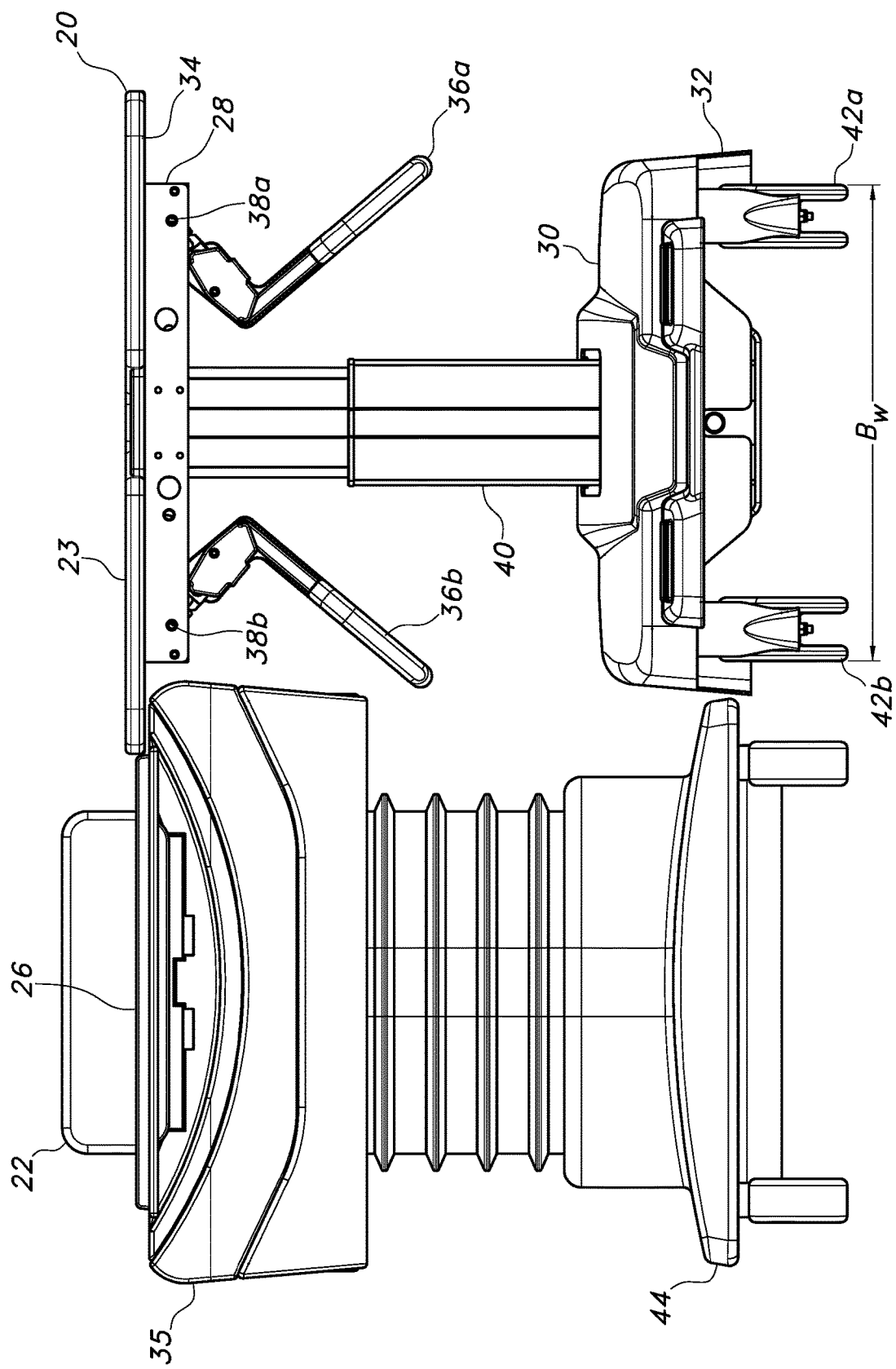
FIG. 2 is a front view of the patient trolley and target modality of FIG. 1.
Figure 3:
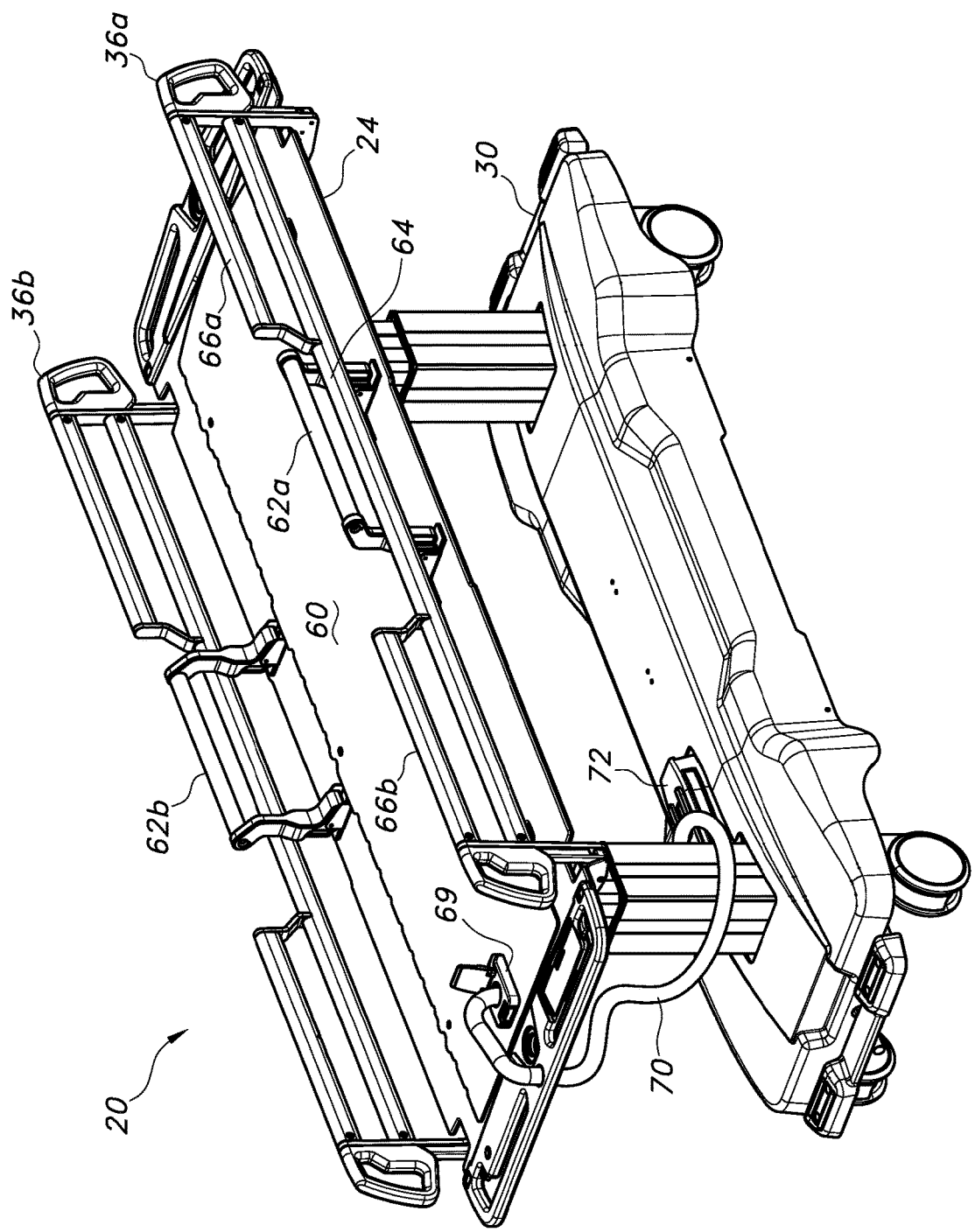
FIG. 3 is a top perspective view of a patient trolley in combination with a patient transfer device according to another embodiment of the present invention.

As seen in FIG. 2, the patient trolley 20 is docked next to the target modality table 22. The top surface 24 of the patient trolley is preferably immediately adjacent to the target patient surface 26 of the target modality table 22. The top surface 24 of the patient trolley 20 is also preferably of the same elevation as the patient support surface 26 of the target modality 22 when the patient trolley 20 is docked. The end handle 23 of the patient trolley may be above the height of the top surface 24, as illustrated in FIG. 2, or of the same or lower elevation. The ability to dock the patient trolley 20, such that the patient support surfaces are immediately adjacent and of approximately equal elevation to each other is possible due to several features of the patient trolley 20.

The top portion of the patient trolley 20 includes a structural element (in this case, a frame) 28 having a lateral width that is much less than the lateral width of the top surface 24 of the trolley. The result is an overhang area 34 that enables the patient trolley 20 to be docked adjacent to target modality 22, such that the overhang area 34 (and the associated top surface 24) are adjacent to the patient support surface 26 of the target modality 22 while maintaining the structural integrity of the trolley top. The overhang area 34 is defined by the longitudinal length of the top surface 24 of the patient trolley and the difference between the lateral widths of the top surface 24 and the structural element 28.

The structural element 28 provides attachment points 38a, 38b for two side rails 36a, 36b. The struts of the side rails 36a, 36b are rotatably attached via a hinge to the structural element 28 on the underside of the top portion of the patient trolley 20. The side rails 36a, 36b may be independently deployed or stowed. In the stowed position, the side rail 36b closest to the target modality 22 is able to swing laterally inboard of the patient trolley 20, such that the side rail 36b does not extend outside of a perimeter of the top surface 24. This configuration provides sufficient space that may be occupied by a portion of the moving table 35 of the target modality table 22. This is particularly advantageous when, for example, the target modality is a medical imaging device.

For example, the moving table 35 may be the portion of the target modality which transports the patient into the active region of an imaging device, also referred to as the gantry or bore. The moving table 35 may slide into the gantry of the target modality. As seen in FIG. 2, the target patient surface 26 of the target modality table 22 is much narrower than the maximum width of the transport section 35. Thus, the space below the overhang area 34 may be occupied by a portion of the moving table 35, thereby enabling the patient trolley 20 to be docked in a position wherein the top surface 24 of the trolley 20 is immediately adjacent to the target patient surface 26 of the target modality table 22. The elevation of the overhang area 34 may be adjusted (described in greater detail below), such that the overhang area 34 is resting on or close to the side portion of the target modality table 22 that is next to the patient support surface 26. As a result, the thickness of the overhang area 34 should be sufficiently thin, so that when the patient trolley 20 is docked, the elevation of the top surface 24 of the patient trolley 20 may be about the same as the elevation of the patient support surface 26 of the target modality table 22.

As explained above, the overhang area 34 is defined by the longitudinal length of the top surface 24 of the patient trolley and the difference between the lateral widths of the top surface 24 and the structural element 28. The overhang area may also be referred to as a perimeter region extending between an outer and inner perimeter. The outer perimeter is the outermost perimeter of the top surface 24 and the inner perimeter is the point at which thickness of the overhang area 34 is no longer a concern. The mounting point(s) of the side rail are preferably inboard laterally from this perimeter region.

Figure 4:
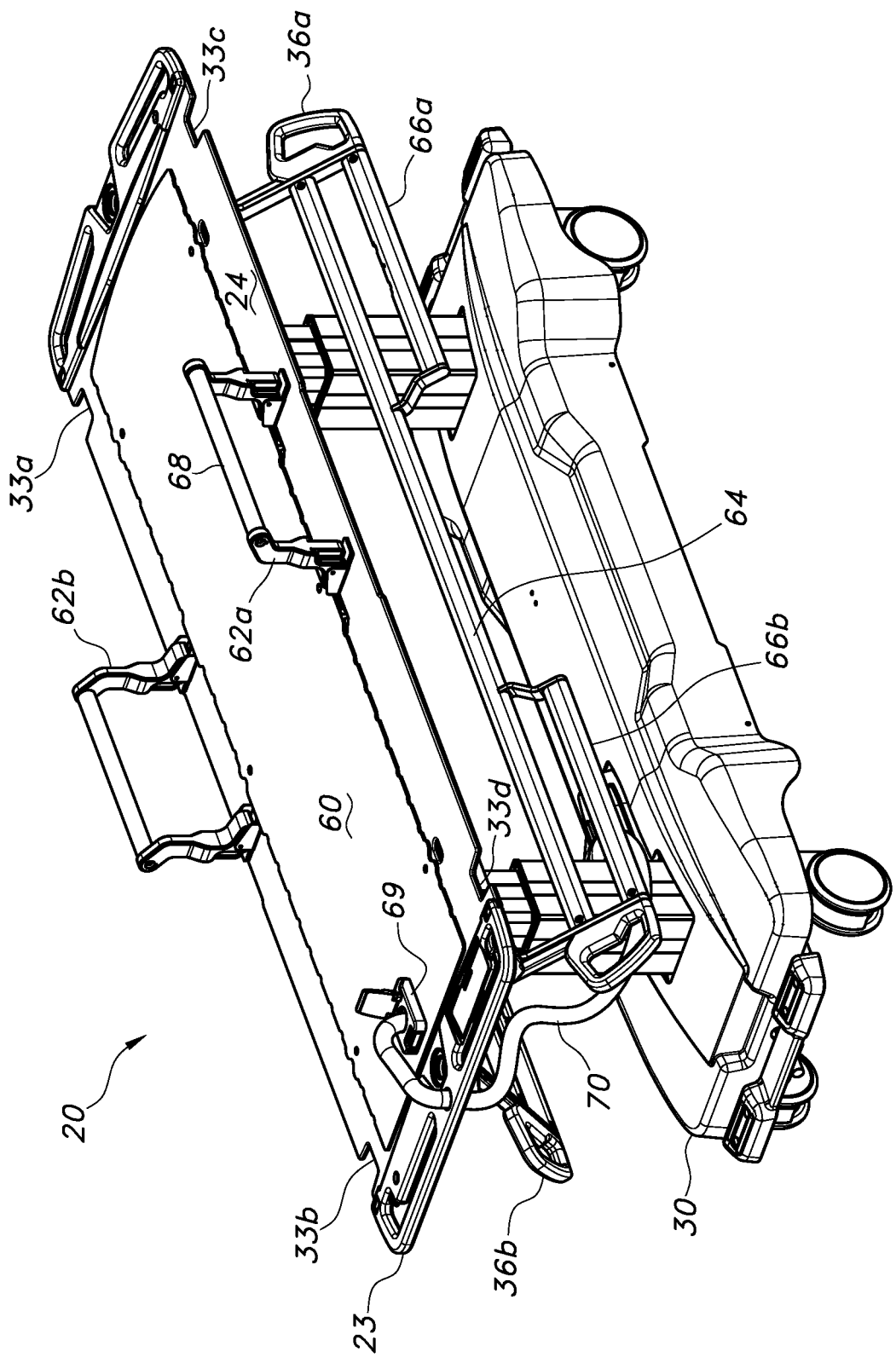
FIG. 4 is a top perspective view of the patient trolley in combination with the patient transfer device of FIG. 3 with the side rails of the patient trolley in a stowed position.
Figure 6:
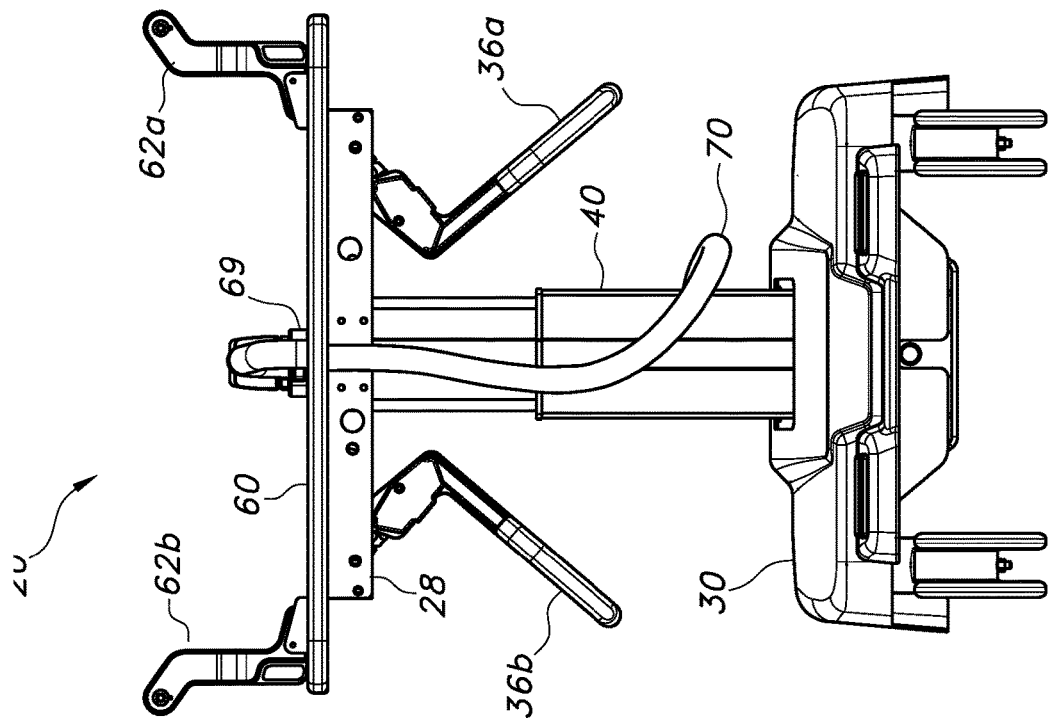
FIG. 6 is a front view of the patient trolley and patient transfer device of FIG. 4.
Figure 5:
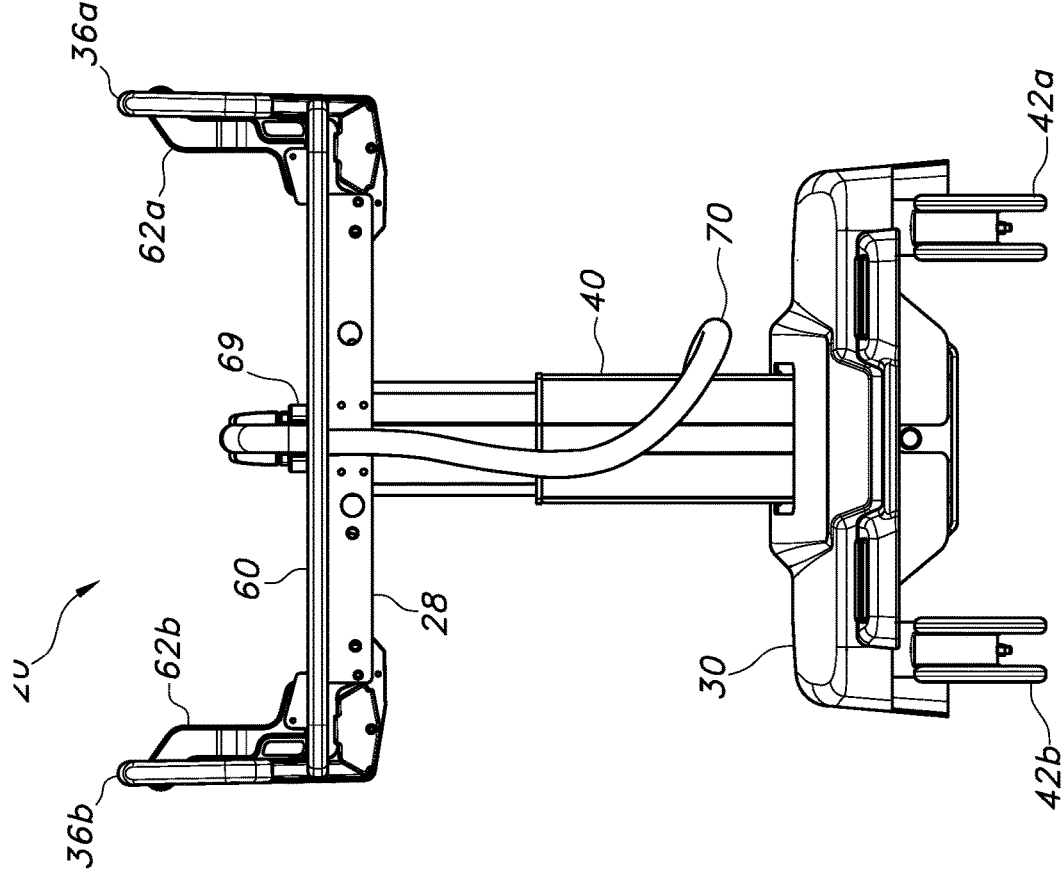
FIG. 5 is a front view of the patient trolley and patient transfer device of FIG. 3.
Figure 7:
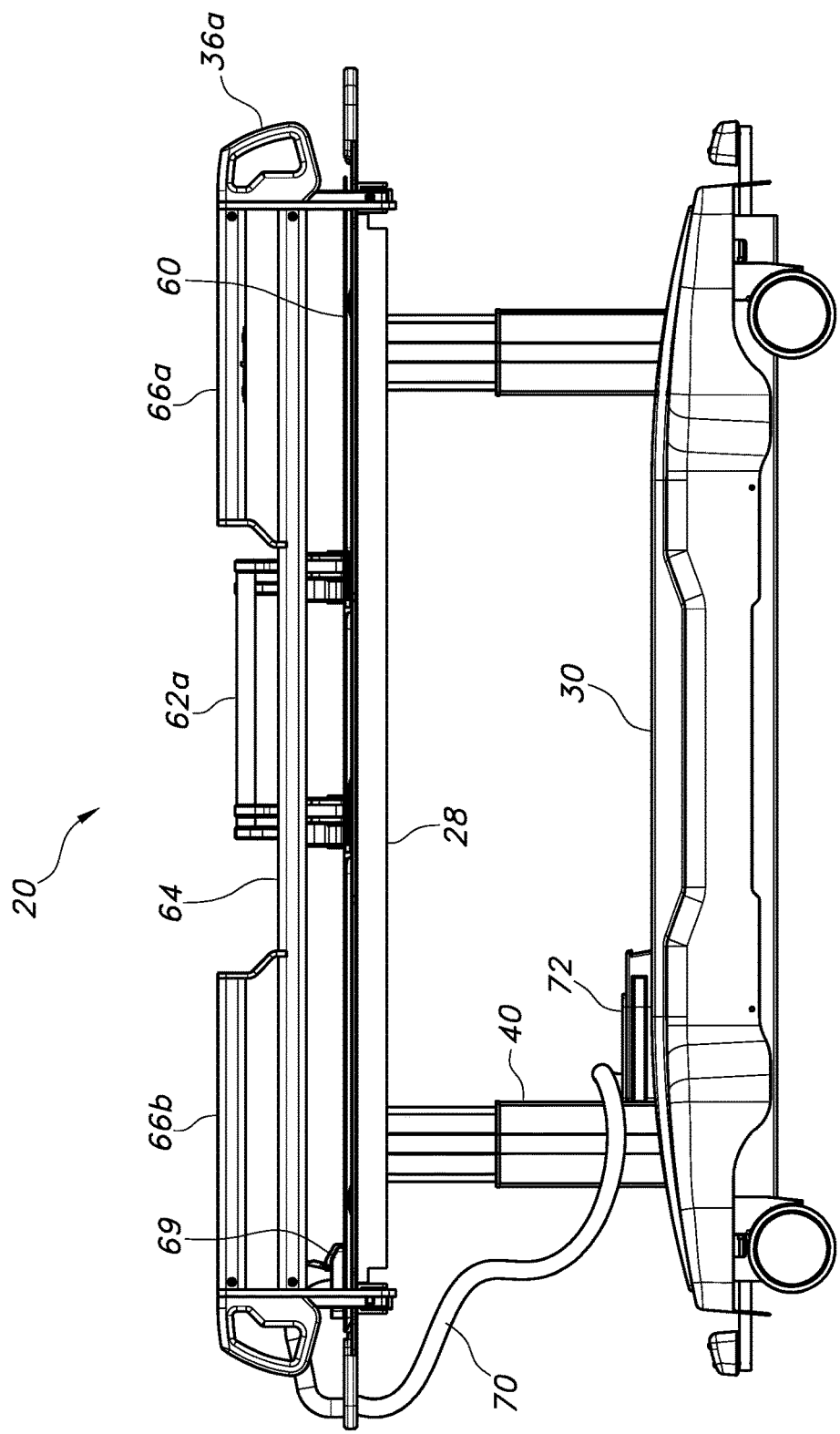
FIG. 7 is a side view of the patient trolley and patient transfer device of FIG. 3.

It is also preferred that the top surface 24 of the patient trolley 20 include recesses 33*a*-*d* along the longitudinal sides of the patient trolley, as illustrated in FIG. 4. The location of the recesses 33*a*-*d* are placed to coincide with the location of the struts when the side rails 36*a*, 36*b* are in the deployed position. The struts of the side rails 36*a*, 36*b* will extend into the recesses 33*a*-*d*, so that the side rails 36*a*, 36*b* do not contribute substantially to the width of the patient trolley 20. The side rails may also include an optional bumper that serve as a protective cover in the event of an impact with a wall or doorway, for example.

By providing recesses for the side rails, available area for a patient on the top surface of the patient trolley according to various embodiments of the present invention is much closer to the overall width of the patient trolley, unlike previously available patient trolleys. For example, the patient trolleys according to the present invention may have a maximum width between the side rails of approximately 32 inches, and the top surface of the patient trolley for supporting a patient may be at least 30 inches, preferably at least 30.5 inches. It is preferred that the side rails add less than 5 cm (2") to the overall width of the system. Thus, the width of the available patient area on the top surface of the patient trolleys according to the present invention is preferably no more than about 5 cm (2") less than the total width of the patient trolley.

The top portion of the patient trolley 20 is attached to the bottom portion 30 of the patient trolley 20 via at least one support. In the embodiment of FIG. 2, the supports are in the form of pillars 40. The pillar may be a fixed pillar, a moving pillar, a hydraulic pillar, a pneumatic pillar, or an electric pillar, for example. The pillars 40 are preferably telescoping to allow adjustment of the height of the top surface 24 of the patent trolley 20, so that when the patient trolley 20 is docked next to a target modality, the elevation of the top surface 24 is lowered or raised to an elevation that is about the same as the height of the target patient surface 26. The bottom portion 30 of the patient trolley includes a plurality of wheels 42*a*, 42*b* that are preferably in the form of casters and include some braking mechanism to lock at least one caster wheel. The lateral wheel base width, $B_w$, between the wheels 42*a*, 42*b* is measured from the outer sides of each wheel. The bottom portion 30 may also include an optional cover 32.

Most commercial trolley or stretcher manufacturers define their wheel base as the distance from the centerline to centerline of the wheels. However, as used herein in the specification and claims, the "wheel base (Bw)" is defined as the outside edge to outside edge of each wheel with the wheels lined up in the longitudinal direction of the trolley. As an example, Hill-Rom® P8000 series stretchers (manufactured by Hill-Rom, Inc. of Batesville, Ind.) have been used as base platforms for patient transport systems. The wheel base listed by the manufacturer is 61 cm (24") as measured between the centerlines of the wheels. However, the outside to outside measurement is greater than 67 cm (26.5").

At the same time, the overall width of trolley systems must be narrow enough to pass through the doorways of typical hospitals and clinics. This means that the maximum width of commercial trollies (with side rails deployed, etc.) is no greater than 91.5 cm (36") and is usually significantly less. For example, 36 inches is the maximum width of a Hill-Rom® P8000 series stretcher. The maximum patient support surface width of a P8000 series stretcher is 76.2 cm (30") (defined by Hill-Rom as the Sleep Deck Width). Based on these numbers, the maximum ratio of the patient support surface to the wheel base for a P8000 series stretcher is 1.13:1. The Diacor Patient Transport Stretcher ZTG-3 (manufactured by Diacor, Inc. of Salt Lake City, Utah) is built on a modified P8000 platform. The patient support surface of that system is 74.3 cm (29.95"), providing a similar ratio.

A preferred embodiment of the present invention comprises a patient support surface of 77.5 cm (30.5") maximum width and a wheel base as defined above of 55.6 cm (21.9"), producing a ratio of about 1.4:1.

In order to dock the patient trolley 20 next to the target modality table 22, bottom portion 30 must be sufficiently narrow so as not to interfere with the target modality base 44. Therefore, the lateral wheel base width, $B_w$, should be sufficiently narrow to accommodate the cover 32, if present. It is also critical that the lateral wheel base width, $B_w$, is not too narrow such that patient trolley 20 is unbalanced and prone to tipping over. Patient trolleys according to the present invention are therefore preferably configured to satisfy the balance requirements of subclause 9.4.3.1 of IEC 60601-1 3rd Edition. As known to those of skill in the art, IEC 60601 is a series of technical standards for the safety and effectiveness of medical electrical equipment, published by the International Electrotechnical Commission. In order to provide a balanced patient trolley having a bottom portion that will not interfere with the base of a target modality table, it is preferred that the ratio of the lateral top width of the top surface of the patient trolley to the lateral wheel base width, $B_w$, is at least 1.2:1, more preferably at least 1.25:1, most preferably 1.35:1. It is also preferred that in some embodiments of the present invention, the lateral wheel base width, $B_w$, of the patient trolley is no greater than 66 cm.

Referring now to FIGS. 3 to 8, a system according to another embodiment of the present invention comprises a patient transfer device 60 on the top surface 24 of a patient trolley 20. The patient transfer device 60 includes a hose connection 69 to receive air from one end of a hose 70. The opposite end of the hose 70 is connected to a hub 72 installed in the bottom portion 30 of the patient trolley 20. The hub 72 may act as a main hub for communication and an air source between the bottom portion 30 and the top surface 24 of the patient trolley 20. The air provided from the hub 72 may deliver air to an air bearing on the underside of the patient transfer device 60 that provides an air bearing which facilitates the transfer of the patient from the top surface 24 of the patient trolley 20 to the target modality. In other preferred embodiments, a separate blower may be mounted to the underside of the patient trolley top and may be used to provide air to a variety of bladders or cushions.

Figure 8:
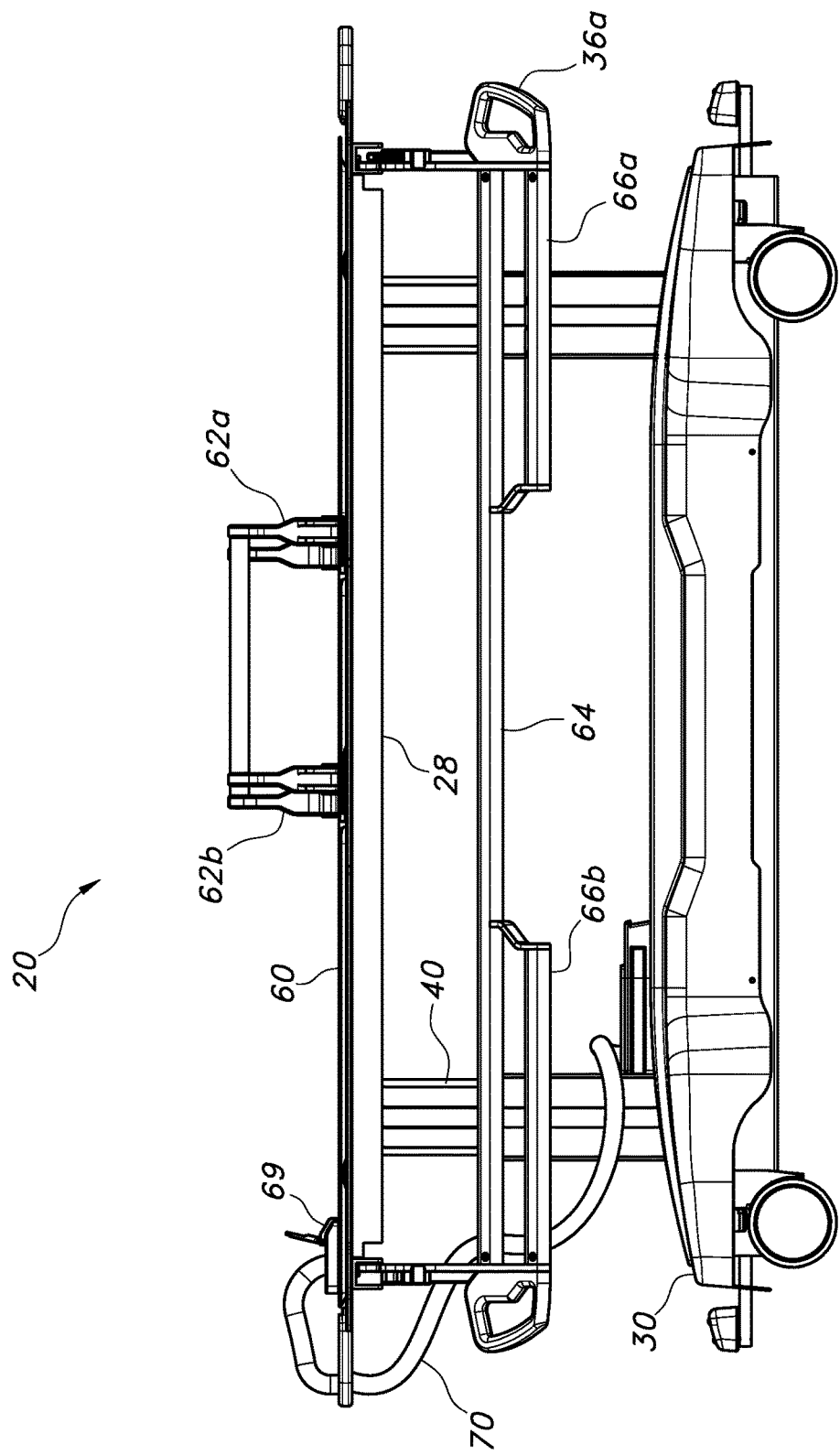
FIG. 8 is a side view of the patient trolley and patient transfer device of FIG. 4.
Figure 12:
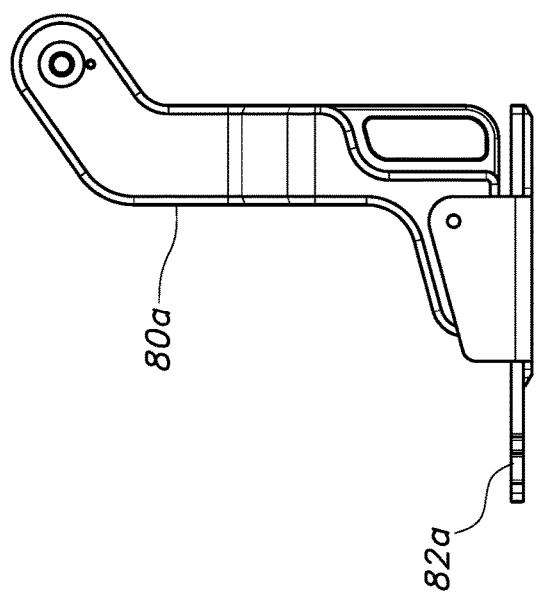
FIG. 12 is a side view of the handle for the patient transfer device of FIG. 9.

The patient transfer device 60 further includes one or more gripping features. The gripping feature may be provided in the form of a post, strap, push surface, handle, or any other form known to those of skill in the art that may be incorporated into the patient transfer device to assist a user in sliding the patient transfer device. The at least one gripping feature preferably includes one or more handles 62*a*, 62*b* removably attached to the patient transfer surface. The handles 62*a*, 62*b* are preferably inserted in about the center of the longitudinal sides of the patient transfer device 60. The handles 62*a*, 62*b* are, therefore, preferably installed such that they are directly across from one another. Alternatively, the handles 62a, 62b may be offset, as illustrated in FIG. 8.

Depending on the location of the patient trolley relative to the target modality, one of the side rails may be lowered to the stowed position while the other side rail remains in a deployed position. Best viewed in FIGS. 3 and 7, a side rail 36a has a maximum height located at any point along longitudinal sections 66a and 66b. A longitudinal section of reduced height 64 is located between the two sections of greater height 66a, 66b. The length of the section of reduced height 64 coincides with the location of the handle 62a of the patient transfer device 60. The reduced height of section 64 is at an elevation which is lower than both the maximum height of the other longitudinal sections 66a, 66b and the height of the handle 62a. In other words, the handle 62a, 62b may have a gripping portion 68 extending to an elevation above the reduced height section 64 of the side rail 36a, which allows access to the handle 62a when the side rail 36a is in the deployed position. The easy access to the handle 62a reduces the potential strain of a user when pushing a patient on the patient transfer device 60 across the top surface 24 of the trolley 20 when transferring the patient to a target modality from the trolley. It also reduces or eliminates the need to move the side rail 36a from the deployed position to the stowed position when manipulating the patient transfer device 60. Leaving the contralateral side rail, i.e. the side on which the user is standing to push the transfer device onto the target modality, in the deployed position provides a safety feature which allows the transfer function to take place while maintaining a barrier against the movement of the patient and/or patient transfer device beyond the longitudinal edge of the top surface 24 of the trolley. The access through a deployed side rail may be achieved in a number of ways, such as a series of posts and gaps, a series of plates, or any other means by which the user's hands may pass over and/or through the side rail to perform the transfer.

Referring now to FIGS. 9-14, an embodiment of a gripping feature according to an embodiment of the present invention is provided as a detachable handle that includes a gripping portion 68. It is preferred that the weight and dimensions of the handle are selected to optimize the ergonomic performance of the handle. For example, the gripping feature of the present embodiment includes a gripping portion that is preferably in the form of a horizontal bar having two vertical supports 80a, 80b located on opposing ends of the horizontal bar. One or both of the vertical supports 80a, 80b may include a locking mechanism 82a. The purpose of the locking mechanism 82a is to ensure that the gripping feature is fixed and secured relative to the patient transfer device 60, so that a patient is safely transferred to the target modality when a user pushes the patient transfer device 60 across the top surface of the trolley.

Figure 13:
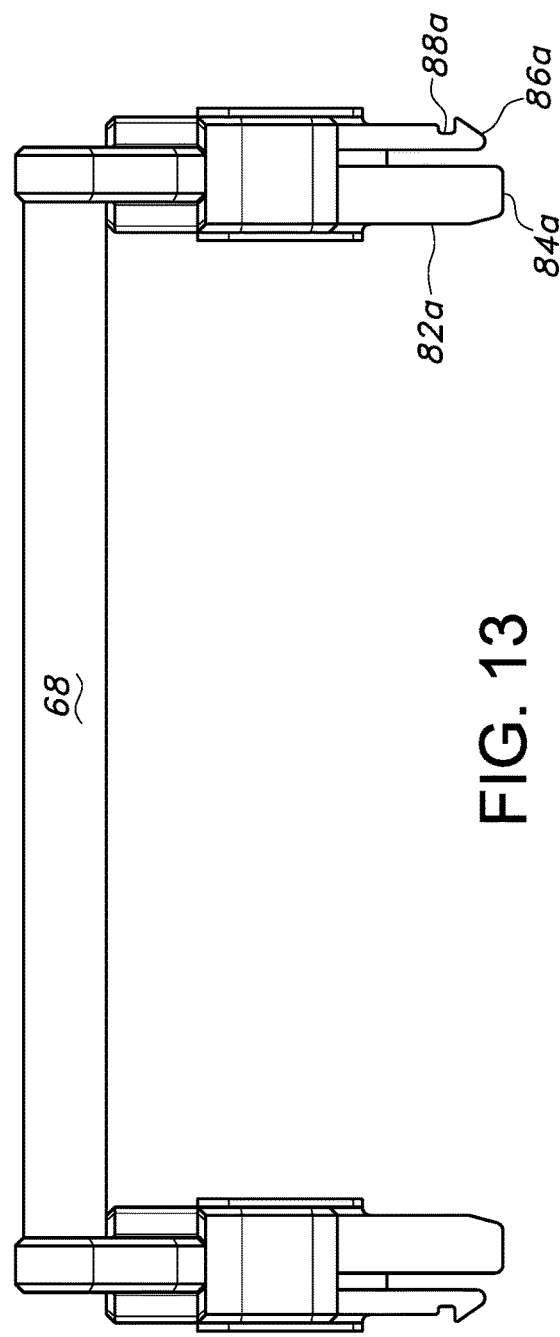
FIG. 13 is a top view of the handle for the patient transfer device of FIG. 9.
Figure 14:
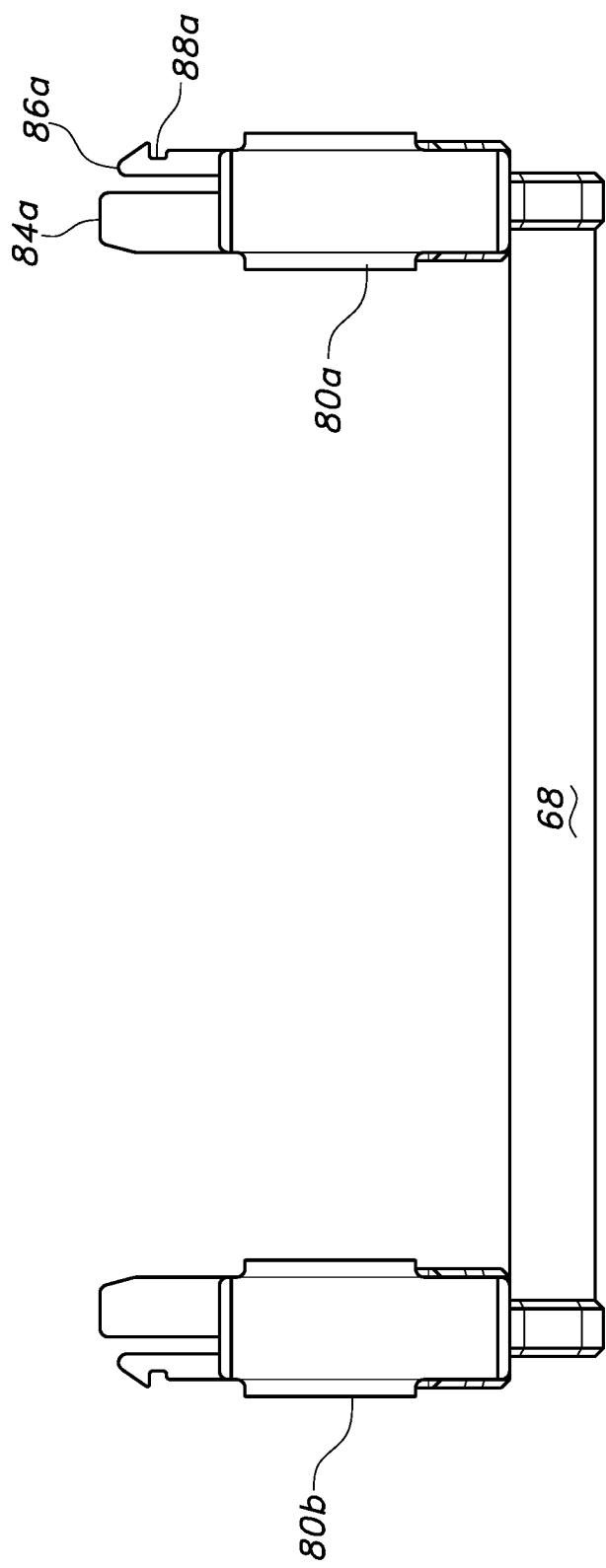
FIG. 14 is a bottom view of the handle for the patient transfer device of FIG. 9.

One embodiment of the locking mechanism 82a, as best viewed in FIGS. 13 and 14, may be in the form of a dual elongated tab or finger design. At least one of the dual fingers is preferably made of resilient material. A gap is provided between a main finger 84a and a resilient minor finger 86a. The minor finger 86a includes a notch 88a present on one side to mate with a corresponding detent, described in greater detail below, in the patient transfer device 60. When inserting the locking mechanisms of the handle into the openings in the side of a patient transfer device, the leading angled edge of the minor finger 86a rides along the detent causing the minor finger 86a to bend across the gap towards the main finger 84a, until the detent reaches the notch 88a. At the point of reaching the notch 88a, the resilient minor finger 86a will return to its original relaxed position, thereby locking the detent in the notch 88a to secure the handle in the patient transfer device. In order to release the gripping feature, a force is applied to the minor finger 86a, so that the minor finger 86a moves across the gap between the main finger 84a and the minor finger 86a. While the minor finger 86a is in the deflected position, the detent is no longer in the notch 88a, and the gripping feature may be removed from the patient transfer device. Upon withdrawing the handle, the minor finger 86a will return to its original relaxed position. Any means known by those of skill in the art may be used as a release mechanism for the locking mechanism. For example, the main finger 84a and minor finger 86a may be attached in a scissor-like fashion. Alternatively, a projection or tab may be included on the minor finger 86a to allow a user to push or pull the minor finger 86a across the gap.

Figure 20:
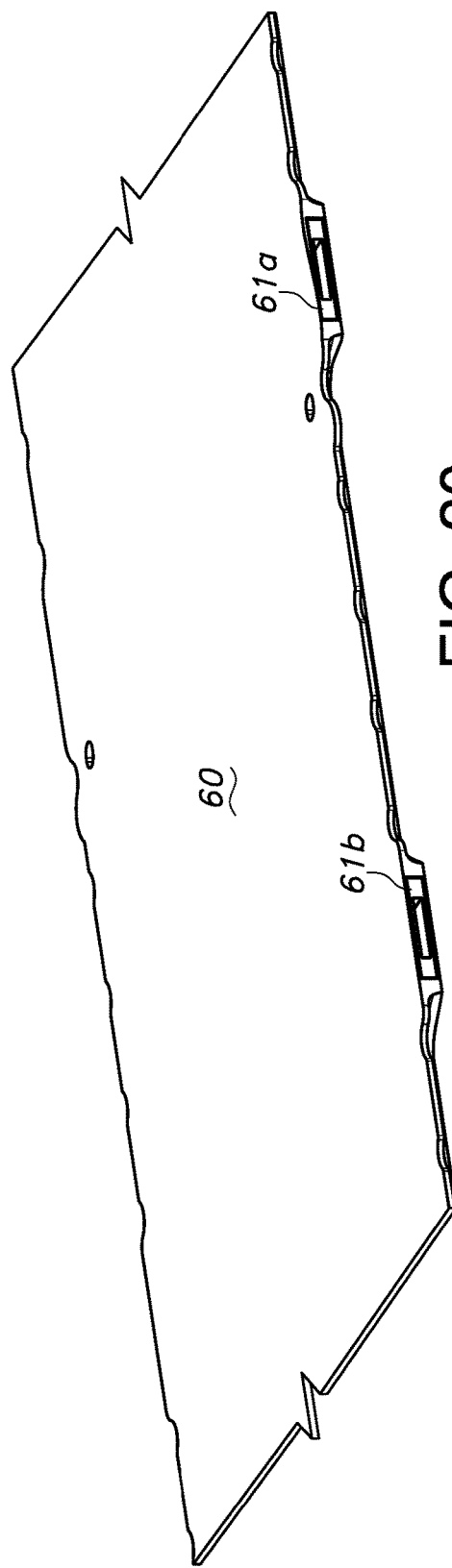
FIG. 20 is a top perspective magnified view of a patient transfer device according to another embodiment of the present invention.

The detent for the locking mechanism may be provided by a locking receptacle 61, as illustrated in FIGS. 17-20. In one embodiment of the invention, the locking receptacle 61 may include a primary opening 63 designed to receive the minor finger 86a and main finger 84a. The width of the primary opening 63 is slightly less than the width of the dual fingers. This will cause the minor finger 86a to deflect towards the gap between the fingers during insertion until the notch 88a reaches a cutout 65a, 65b in the sidewalls of the primary opening 63 of the locking receptacle 61. Upon reaching the cutout 65a, the minor finger 86a will return to its relaxed position and a corner portion 87 of the minor finger 86a will extend into the cutout 65a. The cutout 65a will then serve as a detent preventing withdrawal of the locking mechanism from the locking receptacle 61. The locking receptacles 61a, 61b are preferably symmetrical in order to reduce potential assembly errors when the locking receptacles 61a, 61b are inserted into the sides of the patient transfer device 60, as illustrated in FIG. 20.

According to aspects of this invention, the detachable handle is configured to attach to a side edge of the patient transfer device with a quick disconnect mechanism that can be installed in a thin surface (e.g., under 30 mm). Although the detachable handle is optionally configured to attach to a top surface of the patient transfer device, a patient may be positioned over such a connection and interfere with removal of the handle. Also, although the detachable handle is optionally configured to attach to a bottom surface of the patient transfer device, removal of the detachable handle may be inhibited.

Accordingly, an exemplary embodiment such as the one illustrated in FIGS. 9-14 and 17-20 includes a detachable handle configured to attach to a side edge of the patient transfer device with a quick disconnect mechanism that can be installed in a thin surface of the patient transfer device. By providing a detachable handle, an ergonomic handle may be provided that is removable after transfer, such that the handle will not interfere with subsequent procedures, e.g. advancing the patient into the bore of an MRI or CT scanner, or other medical, diagnostic, treatment, and/or surgical procedures. It is preferred for the patient transfer device to be thin to maximize bore space in scanners and treatment machines (e.g., CT, MRI, Linac, and similar equipment). Such a thin patient transfer device is especially beneficial in MRI environments because the patient should be as close to the table antenna coil of the MRI machine as possible.

The patient transfer device, according to exemplary embodiments, is therefore preferably less than 30 mm in thickness. In one exemplary embodiment, the patient transfer device is about 15 mm thick or less. For these reasons, this invention provides a quick disconnect mechanism to attach a handle (grip) to the edge of a thin, narrow surface.

According to yet another embodiment of the present invention, a patient transfer device is provided that comprises a panel having a top surface, bottom surface, and side extending between the top and bottom surface and a detachable handle having a locking feature attached to a gripping feature, the locking feature being insertable into a receptacle located on at least one of the top surface, bottom surface and side of the panel. The gripping feature may extend away from an area bounded by a perimeter of the top surface of the panel, e.g. a direction normal to the top surface of the panel, so that the handle does not intrude into the space occupied by the patient. The locking feature may be selected from the group consisting of a clasp, a clip, a flexible hook, a pin, a rigid hook, a clamp, and a resilient elongated tab, and the gripping feature may be selected from the group consisting of a cloth loop, a hook, an ergonomic grip, a ring, a knob, a bar, and a strap. The bottom surface of the handle may include a friction reduction surface or feature, such as a skid plate, roller, and bearing, to facilitate patient transfer.

In yet another embodiment of the present invention, a handle for use with a patient transfer device having a receptacle located in at least one of a top surface, bottom surface, and side extending between the top and bottom surface of the panel, is provided. The handle may comprise a detachable locking feature attached to a gripping feature, the locking feature being insertable into the receptacle in an insertion direction and the gripping feature extending from the locking feature in a direction angled with respect to the insertion direction. For example, the gripping feature may extend from the locking feature in a direction perpendicular with respect to the insertion direction.

Figure 15:
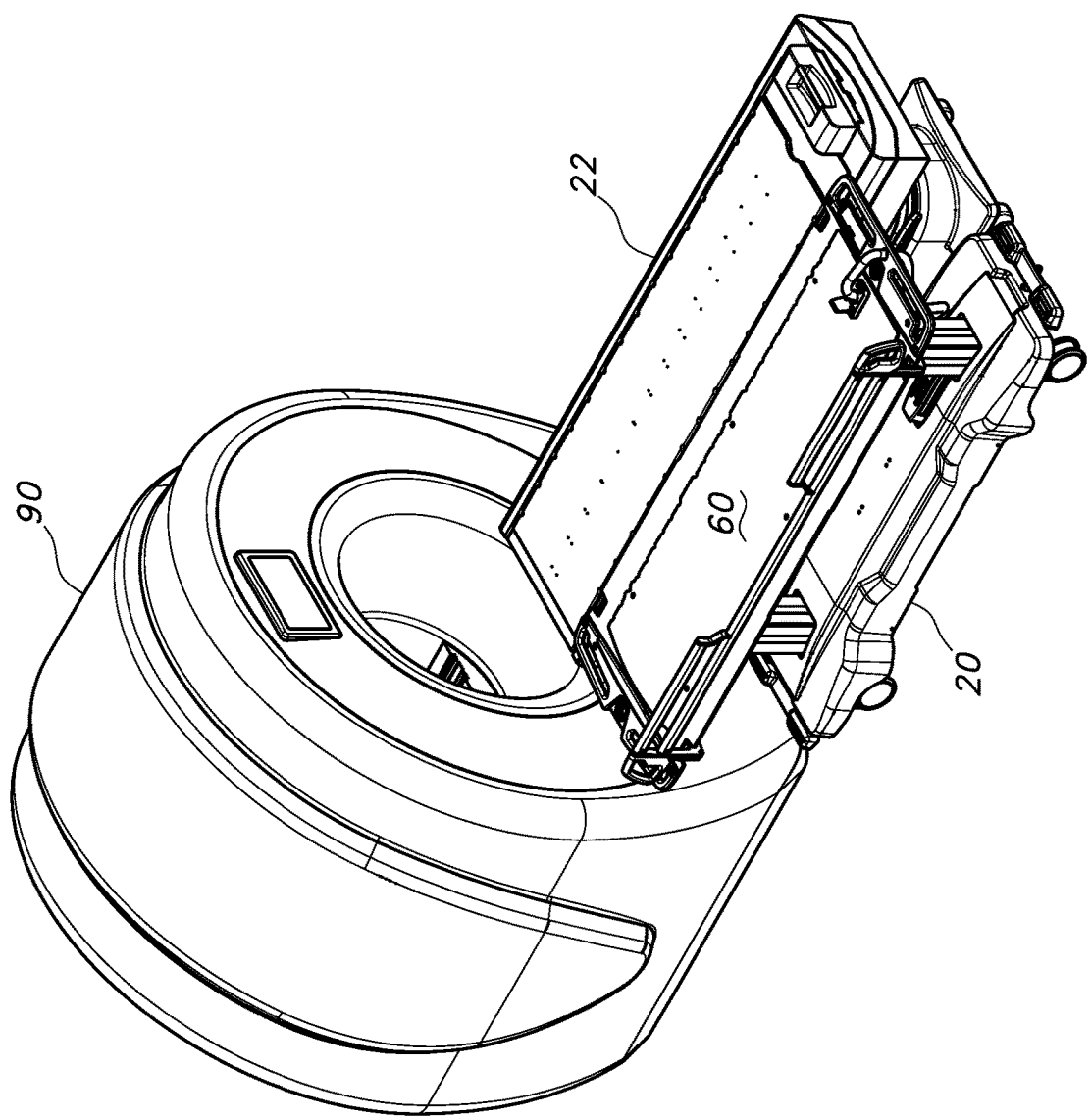
FIG. 15 is a top perspective view of a docked patient trolley and patient transfer device according to another embodiment of the present invention in front of an MRI machine.
Figure 18:
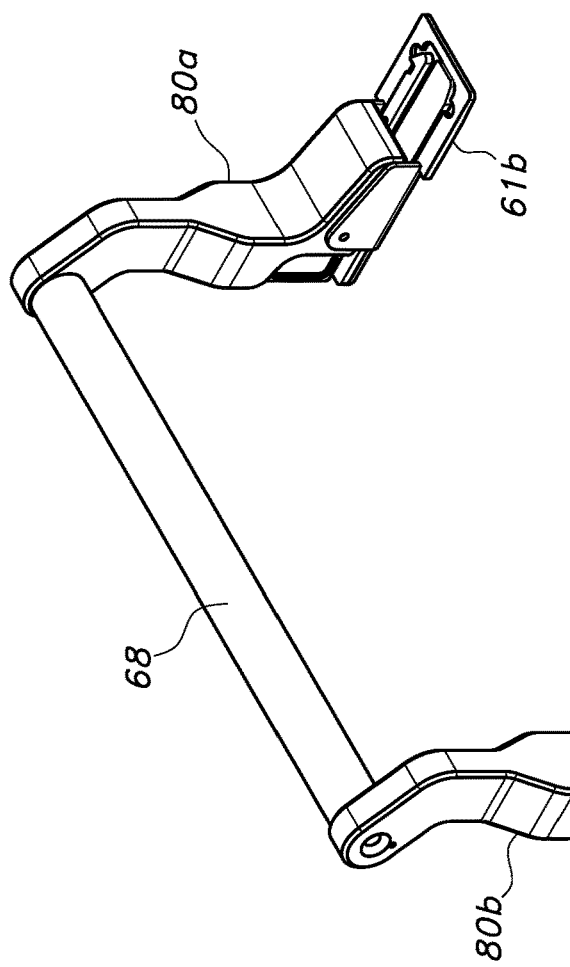
FIG. 18 is a top perspective view of the locking receptacle of FIG. 17 in combination with a handle for a patient transfer device.
Figure 17:
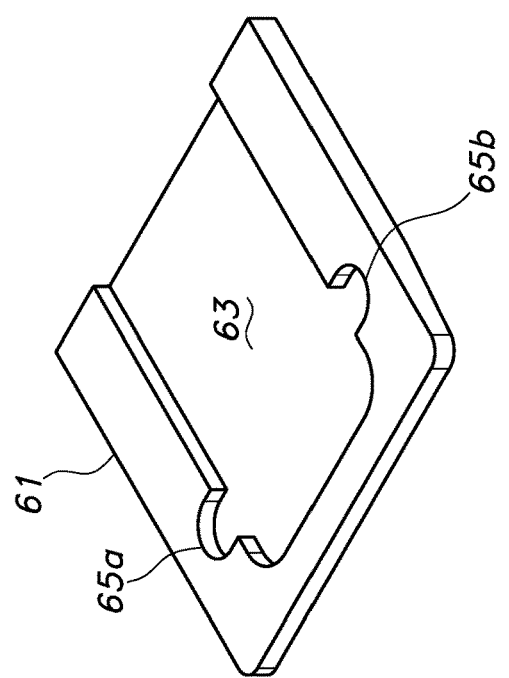
FIG. 17 is a top perspective view of a locking receptacle according to an embodiment of the present invention.
Figure 19:
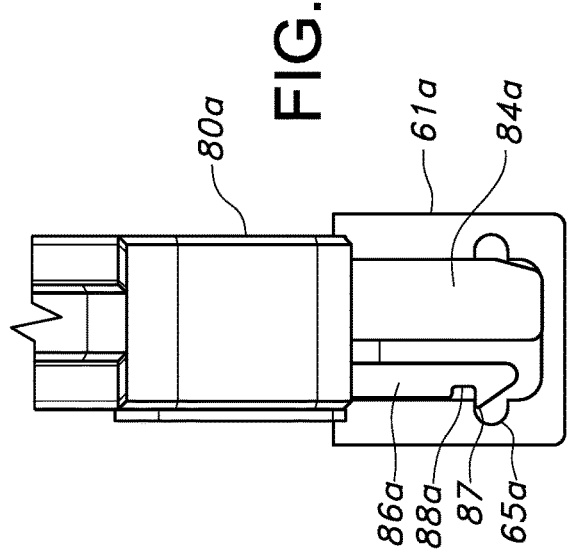
FIG. 19 is a top view of the locking receptacle and a vertical support of the handle of FIG. 18.

According to another aspect of the present invention, a method of docking a patient trolley adjacent a target modality and transferring a patient from the patient trolley to the target modality is provided. With reference to FIGS. 15 and 16, a patient trolley 20 having side rails is shown with a patient transfer device 60 on its top surface. The patient trolley 20 is adjacent to a target modality table 22, which in this example is part of an MRI machine 90.

A first step of the method may include positioning the patient trolley 20 proximate to the target modality, such as the target modality table 22. As explained above, the patient trolley may include a top portion having a top width and a top surface extending across the top width. Prior to docking the patient trolley, at least one side rail, preferably the side rail or side rails closest to the target modality table 22, will be stowed. The stowed position preferably includes lowering the side rail to an elevation below the top surface of patient trolley and inboard laterally such that the side rails is within the top width. When the top surface of the patient trolley 20 is adjacent to the target patient surface of the target modality table 22, such that patient transfer may be accomplished safely, the position of the patient trolley 20 is locked, preferably by engaging a braking mechanism.

The elevation of the top surface of the patient trolley may now be adjusted to generally correspond to an elevation of the support surface of the target modality. Again this may be accomplished by actuating a lift mechanism in the bottom portion of the patient trolley 20. Upon docking a side of the patient trolley adjacent the target modality, an overhang area along the side of the top portion of the patient trolley may be extending over at least a portion of the target modality and adjacent to the target patient support surface of the target modality. As explained above, positioning an edge of the top surface of the top portion of the patient trolley adjacent to an edge of the support surface of the target modality reduces the gap between the two surfaces and assists in transferring the patient easily and safely.

Prior to transferring the patient, a blower (not shown) in the patient trolley 20 may be activated to provide the patient transfer device 60 with an air bearing to reduce friction between the patient transfer device 60 and the surface along which it slides. Alternatively, a low friction interface between the transfer surface and the trolley top/target modality top may be used for transfer such as a low friction surface or surface incorporating wheels or roller bearings. A user may now transfer the patient transfer device 60 by gripping the patient transfer device and transferring the patient transfer device located on the top surface of the top portion of the patient trolley 20 to the patient support surface of the target modality table 22. During transfer, the patient transfer device 60 is contacting at least one of the top surface of the trolley 20 and the support surface of the target modality table 22.

Once the patient transfer device is transferred, a user may now index the patient transfer device to the target modality table 22 or cantilever at least a portion of the patient transfer device in the longitudinal direction of the patient transfer device depending on the needs of the user.

According to one aspect of the invention, a patient trolley is configured for transporting a patient to a target modality and facilitating transfer of the patient from the trolley to a support surface of the target modality, the patient trolley comprising: a top portion having a top width and a top surface extending across the top width, the top portion also having an overhang area along at least one side of the top portion; and a bottom portion supporting the top portion, the bottom portion having a lateral wheel base width narrower than the top width; wherein the top portion is laterally fixed relative to the bottom portion, and wherein the patient trolley is configured to dock adjacent the target modality such that the overhang area is capable of extending over at least a portion of the target modality and adjacent to the patient support surface of the target modality.

According to another aspect of the invention, a method of docking a patient trolley adjacent a target modality prior to transferring a patient from the patient trolley to the target modality is provided, the method comprising: positioning the patient trolley proximate to the target modality, the patient trolley including a top portion having a top width and a top surface extending across the top width; lowering a side rail of the patient trolley to an elevation below the top surface of the top portion of the patient trolley and inboard laterally such that the side rails is within the top width; adjusting an elevation of the top surface of the top portion of the patient trolley to generally correspond to an elevation of the support surface of the target modality; and docking a side of the patient trolley adjacent the target modality such that an overhang area along the side of the top portion of the patient trolley is capable of extending over at least a portion of the target modality and adjacent a support surface of the target modality, thereby positioning an edge of the top surface of the top portion of the patient trolley adjacent an edge of the support surface of the target modality.

According to another aspect of the invention, a patient trolley is configured for transporting a patient to a target modality and facilitating transfer of the patient from the patient trolley to a support surface of the target modality, the patient trolley comprising: a top portion including a top surface and an overhang area along at least one side of the top portion; a side rail coupled to the top portion for movement between a deployed position in which a top of the side rail extends above the top surface of the top portion of the patient trolley and a stowed position in which the top of the side rail is below the top surface of the top portion of the patient trolley and inward from the overhang area of the top portion of the patient trolley; and wherein the patient trolley is configured to dock adjacent to the target modality such that the overhang area is capable of extending over at least a portion of the target modality and adjacent to the support surface of the target modality.

According to another aspect of the invention, a patient transfer system is configured for transporting a patient to and from a target modality and facilitating transfer of the patient to a support surface of the target modality, the patient transfer system comprising: a patient trolley including a top portion having a top surface and an overhang area along at least one side of the top portion, a side rail coupled to the top portion for movement between a deployed position in which a top of the side rail extends above the top surface of the top portion of the patient trolley and a stowed position in which the top of the side rail is below the top surface of the top portion of the patient trolley and inward from the overhang area of the top portion of the patient trolley; and a patient transfer surface located on the top surface of the top portion, the patient transfer surface having at least one gripping feature; wherein the patient trolley is configured to dock adjacent the target modality when the side rail is in the stowed position such that the overhang area is capable of extending over at least a portion of the target modality.

According to another aspect of the invention, a patient transfer system is configured for transporting and facilitating transfer of a patient to a target modality, the patient transfer system comprising: a patient trolley including a top portion having a top width and a top surface extending across the top width, the top portion also having an overhang area along at least one side of the top portion, a side rail coupled to the top portion capable of movement between a deployed position in which a top of the side rail extends above the top surface of the top portion of the patient trolley and a stowed position in which the top of the side rail is below the top surface of the top portion of the patient trolley and inward from the overhang area of the top portion of the patient trolley, and a bottom portion supporting the top portion, the bottom portion having a lateral wheel base width narrower than the top width; a patient transfer device located on the top surface of the top portion, the patient transfer device having at least one gripping feature; and a target modality having a support surface; wherein the patient trolley is configured to dock adjacent to the target modality such that the overhang area is capable of extending over at least a portion of the target modality and adjacent to the support surface of the target modality and facilitate transfer of the patient to the support surface of the target modality.

According to another aspect of the invention, a method of transferring a patient on a patient transfer device from a trolley to a target modality is provided, the method comprising: positioning the patient trolley proximate to the target modality, the patient trolley including a top portion having a top width and a top surface extending across the top width; lowering a side rail of the patient trolley to an elevation below the top surface of the top portion of the patient trolley; adjusting an elevation of the top surface of the top portion of the patient trolley to generally correspond to an elevation of the support surface of the target modality; docking a side of the patient trolley adjacent the target modality such that an overhang area along the side of the top portion of the patient trolley is adjacent to a support surface of the target modality, thereby positioning an edge of the top surface of the top portion of the patient trolley adjacent to an edge of the support surface of the target modality; and gripping the patient transfer device and transferring the patient transfer device located on the top surface of the top portion of the patient trolley to the support surface of the target modality.

According to another aspect of the invention, a patient trolley is configured for transporting a patient to a target modality and facilitating transfer of the patient from the patient trolley to a support surface of the target modality, the patient trolley comprising: a top portion including a top surface and an overhang area along at least one side of the top portion; a side rail coupled to the top portion for movement between a deployed position in which a top of the side rail extends above the top surface of the top portion of the patient trolley and a stowed position in which the top of the side rail is below the top surface of the top portion of the patient trolley and inward from the overhang area of the top portion of the patient trolley; and wherein the top portion includes a recess and the side rail includes a strut that extends into the recess when the side rail is in the deployed position.

According to another aspect of the invention, a patient transfer device is provided comprising: a panel having a top surface, bottom surface, and side extending between the top and bottom surface; and a detachable handle having a locking feature attached to a gripping feature, the locking feature being insertable into a receptacle located on at least one of the top surface, bottom surface and side of the panel.

According to another aspect of the invention, a handle is provided for use with a patient transfer device having a receptacle located in at least one of a top surface, bottom surface, and side extending between the top and bottom surface of the panel, the handle comprising: a detachable locking feature attached to a gripping feature, the locking feature being insertable into the receptacle in an insertion direction and the gripping feature extending from the locking feature in a direction angled with respect to the insertion direction.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed is:

1. A patient trolley configured for transporting a patient to a target modality and facilitating transfer of the patient from the trolley to a support surface of the target modality, the patient trolley comprising:
   a top portion having a top width and a top surface extending across the top width, the top portion also having an overhang area along at least one side of the top portion; and
   a bottom portion supporting the top portion, the bottom portion having a lateral wheel base width narrower than the top width;
   wherein the top portion is laterally fixed relative to the bottom portion;
      wherein the patient trolley is configured to dock adjacent the target modality such that the overhang area is capable of extending over at least a portion of the target modality and adjacent to the patient support surface of the target modality;

the patient trolley further comprising a side rail coupled to the top portion for movement between a deployed position in which a top of the side rail extends above the top surface of the top portion of the patient trolley and a stowed position in which the top of the side rail is below the top surface of the top portion of the patient trolley and inward from the overhang area of the top portion of the patient trolley; and wherein the side rail has a maximum height and a length and at least one section of the length has a reduced height, the reduced height being less than the maximum height, the side rail being configured for accessing a gripping portion of a handle of a patient transfer device when the patient transfer device is positioned on the patient trolley and the gripping portion extends to an elevation above the reduced height section of the side rail.

2. The patient trolley of claim 1, wherein a ratio of the top width to the lateral wheel base width is at least 1.2:1.

3. The patient trolley of claim 1, wherein the lateral wheel base width is at most 66 cm.

4. The patient trolley of claim 1, wherein the patient trolley is configured to satisfy the balance requirements of subclause 9.4.3.1 of IEC 60601-1 3rd Edition.

5. The patient trolley of claim 1, wherein the top portion includes a recess and the side rail includes a strut that extends into the recess when the side rail is in the deployed position.

6. The patient trolley of claim 1, wherein the side rail has a section located laterally inboard from the portion of the target modality underneath the overhang area when the trolley is docked and the side rail is in the stowed position.

7. A patient transfer system comprising:
the patient trolley according to claim 1; and
a patient transfer device positionable on the patient trolley, the patient transfer device comprising:
a panel, and
a detachable handle having a locking feature attached to a gripping feature, the locking feature being insertable into a receptacle located on at least one of the top surface, bottom surface and side of the panel.

8. The patient trolley of claim 1, wherein the top portion comprises a structural element on an underside thereof and the side rail is rotatably coupled to the structural element about a longitudinal axis of the patient trolley.

9. The patient trolley of claim 8, wherein the side rail is rotatably coupled to the structural element at at least one mounting point located inboard laterally from the overhang area.

10. The patient trolley of claim 9, wherein the top of the side rail in the deployed position is at a highest elevation of the side rail, and the top of the side rail in the stowed position is at a lowest elevation of the side rail.

11. A method of transferring a patient on a patient transfer device from a trolley to a target modality, the method comprising:
positioning the patient trolley proximate to the target modality, the patient trolley including a top portion having a top width and a top surface extending across the top width;
lowering a side rail of the patient trolley from a deployed position to a stowed position at an elevation below the top surface of the top portion of the patient trolley;
docking a side of the patient trolley adjacent the target modality such that an overhang area along the side of the top portion of the patient trolley is adjacent to a support surface of the target modality, thereby positioning an edge of the top surface of the top portion of the patient trolley adjacent to an edge of the support surface of the target modality; and
transferring the patient transfer device located on the top surface of the top portion of the patient trolley to the support surface of the target modality;
wherein the method further includes gripping a handle of the patient transfer device at a location where the handle extends to an elevation above a portion of the side rail when the side rail is in the deployed position.

12. A patient trolley configured for transporting a patient to a target modality and facilitating transfer of the patient from the trolley to a support surface of the target modality, the patient trolley comprising:
a top portion having a top width and a top surface extending across the top width, the top portion also having an overhang area along at least one side of the top portion; and
a bottom portion supporting the top portion, the bottom portion having a lateral wheel base width narrower than the top width;
wherein the top portion is laterally fixed relative to the bottom portion, and
wherein the patient trolley is configured to dock adjacent the target modality such that the overhang area is capable of extending over at least a portion of the target modality and adjacent to the patient support surface of the target modality;
the patient trolley further comprising a side rail coupled to the top portion for movement between a deployed position in which a top of the side rail extends above the top surface of the top portion of the patient trolley and a stowed position in which the top of the side rail is below the top surface of the top portion of the patient trolley and inward from the overhang area of the top portion of the patient trolley; and
wherein the patient trolley is configured for use with a patient transfer device positionable on the top surface of the patient trolley, the patient transfer device including a panel and a detachable handle having a locking feature attached to a gripping feature, the locking feature being insertable into a receptacle located on at least one of the a top surface, a bottom surface and a side of the panel;
wherein the gripping feature extends in a direction normal to the top surface of the panel and a bottom surface of the handle includes a friction reduction surface or feature.

13. The patient trolley of claim 12, further configured for use with a patient transfer device comprising
a detachable locking feature attached to a gripping feature, the locking feature being insertable into the receptacle in an insertion direction and the gripping feature extending from the locking feature in a direction angled with respect to the insertion direction.

* * * * *